United States Patent

McKellop et al.

[11] Patent Number: 6,165,220
[45] Date of Patent: Dec. 26, 2000

[54] WEAR RESISTANT SURFACE-GRADIENT CROSSLINKED POLYETHYLENE

[75] Inventors: Harry Alden McKellop, Los Angeles; Fu-Wen Shen, Walnut, both of Calif.

[73] Assignees: The Orthopaedic Hospital; University of Southern California, both of Los Angeles, Calif.

[21] Appl. No.: 09/060,387

[22] Filed: Apr. 14, 1998

Related U.S. Application Data

[63] Continuation-in-part of application No. PCT/US97/18758, Oct. 14, 1997.
[60] Provisional application No. 60/028,355, Oct. 15, 1996.

[51] Int. Cl.[7] .................................. A61F 2/30; A61F 2/32
[52] U.S. Cl. .................................................. 623/18; 623/22
[58] Field of Search ............................... 623/16, 18, 22; 427/2.24, 551; 523/113, 115; 525/937

[56] References Cited

U.S. PATENT DOCUMENTS

| | | | |
|---|---|---|---|
| 4,138,382 | 2/1979 | Polmanteer | 523/113 |
| 4,668,527 | 5/1987 | Fujita et al. | 427/35 |
| 4,743,493 | 5/1988 | Sioshansi et al. | . |
| 5,133,757 | 7/1992 | Sioshansi et al. | . |
| 5,180,394 | 1/1993 | Davidson | 623/18 |
| 5,192,323 | 3/1993 | Shetty et al. | 623/16 |
| 5,236,563 | 8/1993 | Loh | . |
| 5,414,049 | 5/1995 | Sun et al. | . |
| 5,543,471 | 8/1996 | Sun et al. | . |
| 5,577,368 | 11/1996 | Hamilton et al. | . |
| 5,593,719 | 1/1997 | Dearnaley et al. | 427/2.26 |
| 5,609,638 | 3/1997 | Price et al. | 623/181 |
| 5,645,882 | 7/1997 | Llanos | 427/2.24 |
| 5,650,485 | 7/1997 | Sun et al. | . |
| 5,674,293 | 10/1997 | Armini et al. | 623/16 |
| 5,702,448 | 12/1997 | Buechel et al. | 623/16 |
| 5,702,456 | 12/1997 | Pienkowski | 623/18 |
| 5,728,748 | 3/1998 | Sun et al. | . |
| 5,876,453 | 3/1999 | Beaty | 623/16 |
| 5,879,388 | 3/1999 | Pienkowski et al. | 623/18 |
| 5,879,400 | 6/1999 | Merrill et al. | 623/22 |
| 5,879,407 | 3/1999 | Waggener | 623/22 |

FOREIGN PATENT DOCUMENTS

| | | |
|---|---|---|
| 0722973A1 | 7/1996 | European Pat. Off. . |
| 0729 981 A1 | 9/1996 | European Pat. Off. . |
| WO 95/21212 | 8/1995 | WIPO . |
| WO97/29793 | 8/1997 | WIPO . |
| WO 98/01085 | 1/1998 | WIPO . |

OTHER PUBLICATIONS

Appleby, R.W., et al., "Post–gamma irradiation cross–linking of polyethylene tape by acetylene treatment", *J. Material Sci.* 2 9: 227–231 (1994).

Grobbelaar, C.J. et al., "The Radiation Improvement of Polyethylene Prosthesis", *J. Bone & Joint Surgery* 60–B(3): 370–374 (1978).

(List continued on next page.)

*Primary Examiner*—Paul J. Hirsch
*Assistant Examiner*—Michael B. Priddy
*Attorney, Agent, or Firm*—Wean Khing Wong

[57] ABSTRACT

A method for improving the wear resistance of an implant by crosslinking its bearing surface layer, while leaving its non-bearing interior uncrosslinked. Such crosslinking may be achieved by electron-beam irradiation or by chemical crosslinking of the implant. The resulting implant may be further treated to remove the residual free radicals (generated by the electron beam crosslinking process), to remove its most oxidized layer, and/or to stabilize its size. In the case of chemical crosslinking, the resulting implant may be further treated to remove residual chemicals from the crosslinked surface layer.

13 Claims, 17 Drawing Sheets

OTHER PUBLICATIONS

Higgins, J.C., et al., "Evaluation of Free Radical Reduction Treatments for UHMWPE", Prodeedings of the 42nd Annual Mtg, Orthopaedic Res. Soc., Feb. 19–22, at p. 485 (1996).

Jasty, M., et al., "Marked Improvement in the Wear Resistance of a New Form of UHMWPE in Physiologic Hip Simulator", Trans. 43rd Ann. Mtg, Orthopaedic Research Soc., Feb. 9–13, 1997, San Francisco, CA, p. 785.

Jasty, M. et al., "Marked Improvement in the Wear Resistance of a New Form of UHMWPE in a Physiologic Hip Simulator", Trans. Soc. Biomaterials, vol. XX, p. 71, 23rd Ann. Meeting Soc. for Biomaterials, Apr. 30–May 4, 1997, New Orleans, Louisiana, U.S.A., p. 157.

Streicher, R. M., "Investigation on Sterilization and Modification of High Modular Weight Polyethylenes by Ionizing Irradiation", *Beta–Gamma* Jan. 1989, at pp. 34–43.

WEAR RESISTANT SURFACE-GRADIENT CROSSLINKED POLYETHYLENE

This application is a continuation-in-part of a Patent Cooperation Treaty patent application, international application number PCT/US97/18758, entitled "Wear Resistant Surface-Gradient Crosslinked Polyethylene", of Harry A. McKellop, et al., filed on Oct. 14, 1997, which in turn was based on a U.S. provisional application Ser. No. 60/028,355 entitled "Wear-Resistant Polymer", of Harry A. McKellop, et al., filed on Oct. 15, 1996.

TECHNICAL FIELD OF THE INVENTION

The present invention is in the field of medical implants made of polyethylene (PE), in particular, ultrahigh molecular weight PE (UHMWPE) and high molecular weight PE (HMWPE).

BACKGROUND OF THE INVENTION

Ultrahigh molecular weight polyethylene (hereinafter referred to as "UHMWPE") is commonly used to make prosthetic joints such as artificial hip joints. Wear of acetabular cups of UHMWPE in artificial joints introduces many microscopic wear particles into the surrounding tissues. The reaction to these particles includes inflammation and deterioration of the tissues, particularly the bone to which the prosthesis is anchored. Eventually, the prosthesis becomes painfully loose and must be replaced. It is generally accepted by orthopaedic surgeons and biomaterials scientists that the reaction of tissue to wear debris is the chief cause of long-term failure of such prostheses.

The literature describes numerous attempts to improve the wear resistance of polyethylene (hereinafter referred to as "PE") in joint replacements. Grobbelaar et al. [*J. Bone & Joint Surgery*, 60-B(3): 370–374 (1978)] attempted to improve the cold-flow characteristics of "high-density" PE prostheses made of Hostalen RCH 1000 C, without sacrificing its low-frictional properties, through a process of radiation crosslinking. Grobbelaar et al crosslinked the PE using high penetration gamma radiation in the presence of crosslinking gases, including acetylene and chlorotrifluoroethylene, or in an inert nitrogen atmosphere. Due to the absorption of the crosslinking gasses, the surface was more crosslinked than the interior of the polyethylene. Nevertheless, because of the high penetration power of gamma radiation, the PE became crosslinked throughout.

To improve the wear resistance of a medical prosthetic device, Farrar, WO 95/21212, used plasma treatment to crosslink its wear surface. This wear surface comprises a plastic material such as UHMWPE. Crosslinking was assumed to have occurred based on the presence of Fourier transform infrared (FTIR) absorption bands at 2890 $cm^{-1}$. Farrar claims his ATR (attenuated total reflection) data imply that he had achieved a penetration depth of 0.5 microns, but the degree of crosslinking is not disclosed.

Streicher, *Beta-Gamma* 1/89: 34–43, used high penetration gamma radiation or high penetration (i.e., 10 MeV) electron beam radiation to crosslink UHMWPE and HMWPE specimens throughout their entire thickness. Streicher annealed the gamma irradiated material in a nitrogen atmosphere in order to increase crosslinking and reduce oxidation during long-term storage. Streicher found that the wear of the materials was greater after the crosslinking by electron beam radiation.

Higgins et al [Transactions of the 42nd Ann. Mtg., Orthopaedic Res. Soc., Feb. 19–22, 1996, p. 485] attempted to stabilize UHMWPE against oxidation after high penetration gamma irradiation (which crosslinked their specimens through the entire thickness) by reducing the concentration of free radicals. They used the following post-irradiation treatments: (1) pressurizing in hydrogen at 15 psi for 2 hours, or (2) heating at 50° C. for 182 hours. They compared the amount of free radicals remaining in the PE using electron spin resonance (ESR), but they did not assess the impact of these treatments on the mechanical or wear properties of the UHMWPE, nor on the oxidation resistance.

SUMMARY OF THE INVENTION

One aspect of the invention presents surface-gradient crosslinked PE and medical implants having surface-gradient crosslinked PE which are wear resistant. The PE is preferably UHMWPE or HMWPE. The most preferred implant is an acetabular cup. The PE and implants may be made by the methods described below.

Another aspect of the invention presents a method for improving the wear resistance of the bearing surface of an implant. The implant or its bearing surface is made of PE, preferably UHMWPE or HMWPE. In one embodiment, the method comprises exposing the implant to an electron beam (the term "electron beam" is hereinafter referred to as "e-beam") radiation with an energy level specifically selected to crosslink the bearing surface of the implant to improve the wear resistance only to a depth sufficient such that the crosslinked layer will not be worn through during the life of the patient, while leaving the remainder uncrosslinked, thereby avoiding any reduction in mechanical properties that otherwise result from crosslinking. Additionally, confining the crosslinking to a thin surface layer facilitates neutralizing free radicals and/or extracting residual chemicals.

In another embodiment of the invention, instead of crosslinking the bearing surface with e-beam radiation, the bearing surface of the implant is crosslinked to a limited depth with a free radical generating chemical, again while leaving the remainder of the implant uncrosslinked for the reasons mentioned above. The free radical generating chemical is preferably a peroxide.

In both of the above methods, the crosslinking is preferably in the surface layer, gradually decreasing to nearly zero in the interior of the PE.

With e-beam crosslinking, it is preferable that the implant be packaged in a low oxygen atmosphere during irradiation, such as an inert gas (e.g., nitrogen) or a vacuum, in order to minimize oxidation and maximize crosslinking of the surface layer. However, if an implant is e-beam irradiated while in air, the outer layer of the bearing surface may then be removed, e.g., by machining, to eliminate the more oxidized and less crosslinked material. In such a case, the depth of crosslinking penetration of the e-beam can be increased to take into account the thickness of material to be removed.

It is preferable that the surface-crosslinked material be treated to eliminate residual free radicals generated by the crosslinking process in order to stabilize it against long-term oxidation. This can be achieved by one or more of the following methods: (1) remelting the partially formed crosslinked material after crosslinking irradiation but prior to final shaping of the implant, (2) annealing the partially formed crosslinked material or the final shaped implant, (3) exposing the crosslinked material or implant to pressurized hydrogen and/or (4) treating the implant using ethylene oxide.

With chemical crosslinking, the implant may be annealed after crosslinking to stabilize its size. In addition, the implant may be soaked in suitable solvents to extract from the crosslinked surface layer any residual chemicals, resulting from decomposition of the free radical generating chemical, in order to minimize leaching out of such chemicals during in vivo use, and to minimize long-term oxidation of the crosslinked material.

Figure 1:
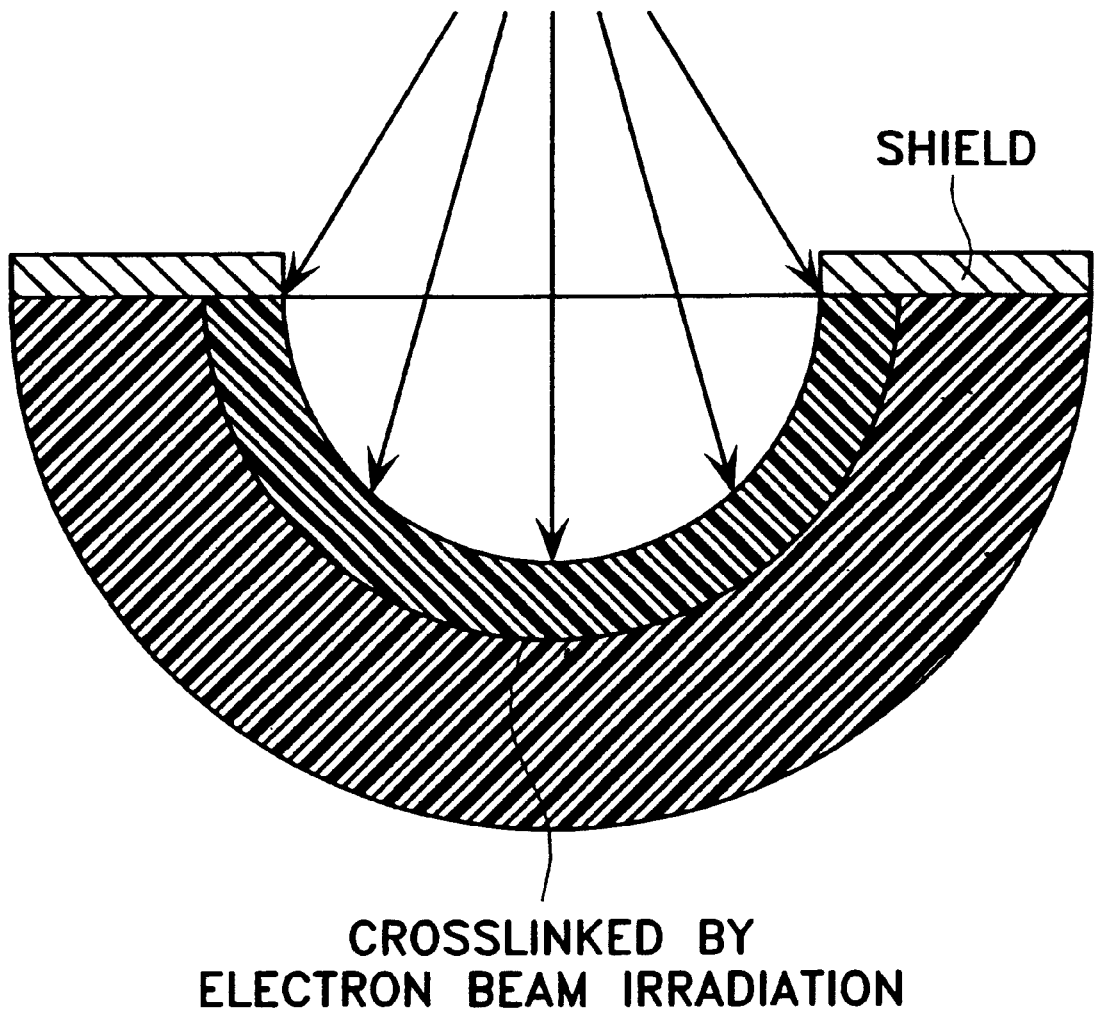
FIG. 1 schematically shows an UHMWPE acetabular cup being exposed to e-beam radiation. A thin shield of steel or other suitable material may be placed over those regions where crosslinking is not desired (e.g., the non-bearing surfaces).

DETAILED DESCRIPTION OF THE INVENTION (I) Implants of the Present Invention

Chemical crosslinking of UHMWPE has been proven to substantially reduce the wear of UHMWPE hip acetabular cups when tested in a wear simulator. EP 0722973 A1, "Chemically Crosslinked Ultrahigh Molecular Weight Polyethylene for Artificial Human Joints" of R. Salovey, et al., published Jul. 24, 1996. In addition, appropriate amounts of crosslinking induced by gamma radiation or e-beam radiation, which crosslinked the entire bulk of an UHMWPE specimen, produced comparably low wear rates (WO 98/01085 of Fu-Wen Shen et al.; Jasty, M., et al., "Marked Improvement in the Wear Resistance of a New Form of UHMWPE in Physiologic Hip Simulator", Transactions of the 43rd Ann. Mtg, Orthopaedic Research Society, p. 785, Feb. 9–13, 1997, San Francisco, Calif.).

However, crosslinking a PE may adversely affect its other physical properties, resulting in reductions in one or more of the following: Young's modulus, impact strength, fatigue strength, yield stress, tensile strength at break, and elongation at break. These reductions may, in turn, negatively affect the overall in vivo performance of an implant made from the crosslinked PE. Thus, a method which improves the wear resistance of the bearing surface of a PE implant, while minimizing the reduction in these mechanical properties in the bulk of the implant, would be advantageous, especially for use in medical implants (hereinafter abbreviated as "implants").

Since the clinical wear rate of conventional UHMWPE used in making acetabular cups for hip replacement, as reported in various studies in the literature, averages about 100 to 200 microns per year, and since appropriately crosslinked UHMWPE (e.g., chemically or radiation crosslinked UHMWPE of EP 0722973 A1, and WO 98/01085, above) exhibits a twenty-fold or lower wear rate, then an appropriately crosslinked UHMWPE can be expected to wear about only 5 to 10 microns/year in typical clinical use. Applicants realized that, at this lower wear rate, about 100 to 200 years would be required to wear through a one-millimeter (i.e., 1000 micron) thick surface layer of crosslinked UHMWPE, i.e. far longer than the life expectancy of the patient.

Thus, one aspect of the invention presents a new surface-gradient crosslinked PE, or an implant with surface-gradient crosslinked PE. These PE and implants are more wear resistant in the crosslinked surface layer than their uncrosslinked counterparts, while maintaining the good physical properties in the bulk of the implant. The PE is preferably HMWPE and/or UHMWPE. The bearing surface of the implant, which may include any surface which is susceptible to wear, is appropriately crosslinked, with the crosslinking preferably gradually diminishing, preferably to zero crosslinking, below this layer to provide a gradual transition of physical properties to those of the conventional HMWPE or UHMWPE. The gradual transition is preferred so that there is not a weak interface that could delaminate, i.e., due to a sudden change from crosslinked to non-crosslinked material.

While it is most preferable to crosslink the intended bearing surface, e.g., the inner concave surface of an acetabular cup which articulates against the opposing femoral ball, it may be desirable also to crosslink any surface which is susceptible to wear due to moving contact with another surface (e.g., in a sliding, pivoting, or rotating relationship to one another), whether or not such motion is intended, such as the backside of a UHMWPE liner of a hip acetabular cup where it presses against the inside of the metal shell. Thus, the term "bearing surface" may also include any surface which is susceptible to wear or for which a user desires to improve its wear resistance.

Thus, for a particular implant made of PE, the depth of crosslinking in the bearing surface is preferably at or more than the thickness of the PE which would be worn away in a patient's lifetime. For example, the implant may have a maximum gel content of from about 80 to about 100% (more preferably from about 90 to about 100%, and most preferably about 95%) within the bearing surface, which gradually decreases to about 50% of the maximum value at about 0.5 mm to about 2 mm from the surface of the implant, and tapering to nearly zero by about 2 mm to about 2.5 mm from the surface of the implant. These ranges are particularly suitable for an acetabular cup, where the bearing surface is its inner bearing surface and/or the backside of the acetabular cup where it presses against the inside of the metal shell; these ranges will leave the core of the acetabular cup nearly uncrosslinked.

Examples of the methods for achieving such surface-gradient crosslinked PE and implants are set forth below. Clearly, one skilled in the art will realize that such implants and PE can also be made by other crosslinking methods known in the art and modified, according to the teaching presented herein, to produce such materials.

The preferred PE for use in the present invention generally possesses molecular weight of about $10^5$ grams per mole or greater. The PE are generally between about $4 \times 10^5$ to about $10^7$ grams per mole. HMWPE and UHMWPE are preferred. HMWPE have molecular weights ranging from about $10^5$ grams per mole to just below $10^6$. UHMWPE have molecular weights equal to or higher than $10^6$ grams per mole, preferably from $10^6$ to about $10^7$.

For implants, the preferred PE are those that are wear resistant and have exceptional chemical resistance. UHMWPE is the most preferred PE, as it is known for these properties and is currently widely used to make acetabular cups for total hip prostheses and components of other joint replacements. Examples of UHMWPE are those having a molecular weight ranging from about 1 to $8 \times 10^6$ grams per mole, examples of which are: GUR 4150 or 4050 (Hoechst-Celanese Corporation, League City, Tex.) with a weight average molecular weight of 5 to $6 \times 10^6$ grams per mole; GUR 4130 with a weight average molecular weight of 3 to $4 \times 10^6$; GUR 4120 or 4020 with a weight average molecular weight of 3 to $4 \times 10^6$; RCH 1000 (Hoechst-Celanese Corp.) with a weight average of molecular weight of $4 \times 10^6$ and HiFax 1900 of 2 to $4 \times 10^6$ (HiMont, Elkton, Md.). Historically, companies which make implants have used PE such as HIFAX 1900, GUR 4020, GUR 4120 and GUR 4150 for making acetabular cups.

The surface-gradient crosslinked PE and implants are useful as prostheses for various parts of the body, such as components of a joint in the body. For example, in the hip joints, they can be a prosthetic acetabular cup (as exemplified above), or the insert or liner of the cup, or a component of a trunnion bearing (e.g. between the modular head and the stem). In the knee joint, they can be a prosthetic tibial plateau (femoro-tibial articulation), patellar button (patello-femoral articulation), and trunnion or other bearing components, depending on the design of the artificial knee joint. For example, in knees of the meniscal bearing type, both the upper and lower surfaces of the UHMWPE component may be surface-crosslinked, i.e., those surfaces that articulate against metallic or ceramic surfaces. In the ankle joint, they can be the prosthetic talar surface (tibio-talar articulation) and other bearing components. In the elbow joint, they can be the prosthetic radio-humeral joint, ulno-humeral joint, and other bearing components. In the shoulder joint, they can be used in the glenoro-humeral articulation, and other bearing components. In the spine, they can be used in intervertebral disk replacement and facet joint replacement. They can also be made into temporo-mandibular joint (jaw) and finger joints. The above are by way of example, and are not meant to be limiting.

For ease of discussion, the following often uses UHMWPE and acetabular cup implants as examples of PE and implants, respectively. However, it is to be understood that the present invention would be applicable to PE in general; and to implants in general.

(II) E-beam Crosslinking

In one aspect of the invention, the bearing surface of the UHMWPE cup is crosslinked using e-beam irradiation. The higher the energy of the e-beam, the deeper the penetration into the PE and, thus, the deeper the resultant crosslinking. A 10 MeV e-beam, such as used by Streicher and by Jasty, M., et al., above, and commercially used, would penetrate about 40 to 50 millimeters of a UHMWPE specimen.

In contrast, the present invention uses an e-beam with an energy of much less than 10 MeV, and preferably less than about 1 MeV. For example, in EXAMPLE 1, below, 0.875 and 0.650 MeV were used. With MeV in this lower range, the bearing surface of an acetabular cup can be rendered more wear resistant to a sufficient depth that it will not be worn through in the patient's lifetime, while keeping the rest of the acetabular cup non-crosslinked to retain the excellent mechanical properties of the conventional UHMWPE.

The e-beam dose in the surface layer to be crosslinked is preferably from about 1 to about 25 Mrad, more preferably from about 5 to about 15 Mrad, and most preferably about 10 Mrad. The dose preferably gradually tapers off to about 50% of the maximum value at about 0.5 mm to 2 mm into the cup. For example, a 10 Mrad may be applied in the bearing surface layer of the cup, the radiation dose gradually tapering off to 50% of the maximum value, i.e., 5 Mrad, at a depth of about 1 mm, and finally tapering to zero at a depth of 2 mm into the cup.

During crosslinking with e-beam, the UHMWPE cups or partially formed cups (e.g.,of Methods 1 to 3, below) may be enclosed in a low-oxygen atmosphere, e.g., of inert gas, such as nitrogen, or in vacuum, to minimize oxidation of the surface layer during irradiation.

Figure 4:
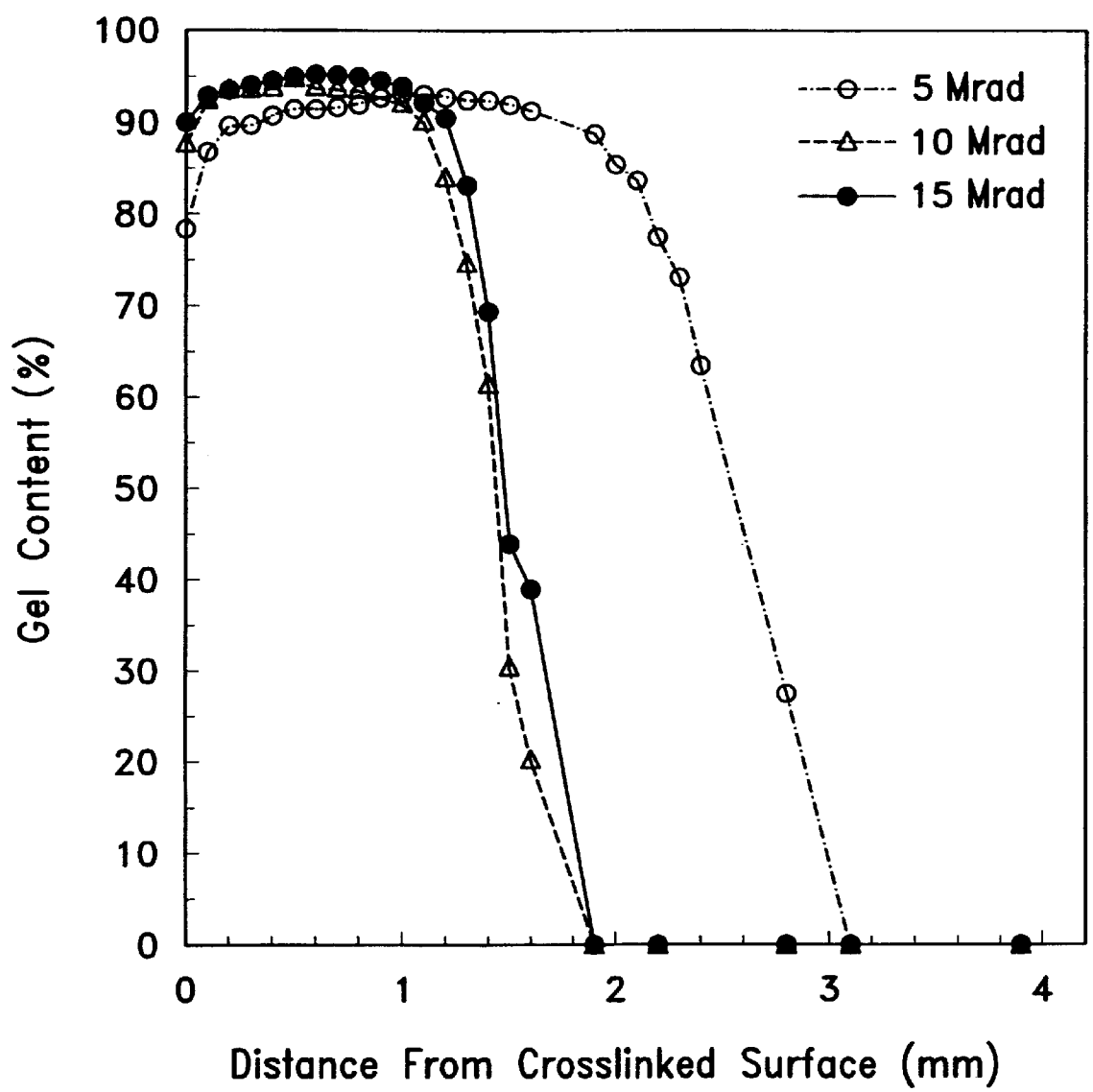
FIG. 4 graphically presents the gel content vs distance from the e-beam crosslinked surface of UHMWPE specimens.

In addition, particularly for cups irradiated in air, the implant can initially be fabricated slightly oversize and then, after irradiation and treatment to reduce the residual free radicals, the outermost surface layer (e.g., a few hundred microns, such as 100 to 300 microns) in the bearing region can be machined away to remove the most oxidized material, which typically has a reduced wear resistance compared to the less oxidized material immediately beneath this layer. In this case, the depth of the initial crosslinking would be increased, such that, after the oxidized surface is machined away, the remaining crosslinked layer would be of the desired thickness. The thickness of the most oxidized surface layer to be removed can be determined for a given process, for example by determining its gel content profiles using the method as shown in EXAMPLE 1, and producing a graph similar to that of FIG. 4, which shows the depth of the lower gel content (least crosslinked) region near the irradiated surface.

Ethylene oxide treatment, e.g., using methods known in the art for ethylene oxide sterilization of implants, has the additional benefit of decreasing the susceptibility to oxidation of e-beam irradiated PE (and, thus, increasing its long term wear resistance, see e.g., EXAMPLE 4, below) by reducing any residual free radicals resulting from e-beam radiation. The duration of ethylene oxide treatment may be shortened or extended according to the desired amount of free radicals to be reduced.

The following provides three non-limiting examples for carrying out the crosslinking process:

Method 1: E-beam Irradiation of an Acetabular Cup

Figure 13:
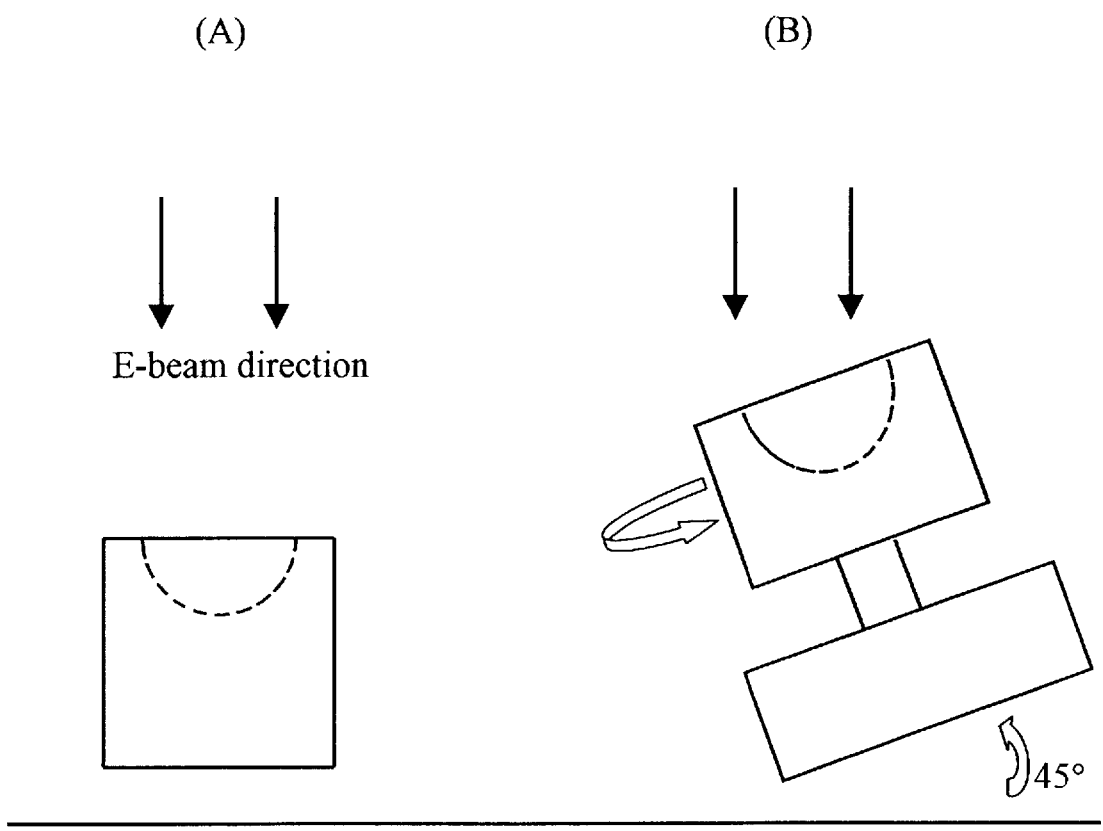
FIG. 13 schematically presents the direction of electron beam radiation for: (A) a specimen placed flat on a table; and (B) a specimen mounted on a rotary motor tilted at an angle of 45 degree.

In this method, an acetabular cup is irradiated with e-beam at room temperature to produce gradient-surface crosslinking on its bearing surface. With curved bearing surfaces, such as the inner concave surface of the acetabular cup, several methods may be used to distribute the dose of crosslinking over the entire bearing surface more uniformly. For example, the implant may be exposed to the e-beam in several passes, with the implant re-positioned between each partial irradiation in order to produce a more uniform distribution over the entire bearing surface. Alternatively, the implant may be rolled through the beam, such that the dose is spread more uniformly around the exposed surface. EXAMPLE 5, below shows other methods of irradiating the cups, such as placing a cup on a stationary flat surface at a 90 degree angle incident to the e-beam [FIG. 13(A)] or having the e-beam scan the cup at an angle and crosslinking the cup throughout its surface, such as can be achieved by rotating the cup and keeping it at an angle of 45 degrees incident to the e-beam as shown in FIG. 13(B). It should be noted that it is not essential that the profile of crosslinking be uniform throughout the wear surface of the cup. It is only necessary that the points on the cup surface which are most susceptible to wear, have an adequate crosslinking profile. Whichever technique is used, the appropriate combination of beam oscillation angle and exposure time to produce the desired dose in the surface layer of the implant can be calculated by one skilled in the art. Such techniques are routinely applied in the e-beam industry for producing aseptic packaging, for example, on the interior surfaces of beverage containers.

Since it may be desirable to crosslink only the bearing surfaces, a shield (e.g., a metal such as steel) may be placed over those areas of the cup that are not intended to be crosslinked, to shield them from the e-beam. Although FIG. 1 schematically shows an abrupt boundary between the crosslinked surface layer and the non-crosslinked material, in practice this is preferably a gradual transition to uncrosslinked material beneath the surface layer.

In order to minimize long-term oxidation caused by residual free radicals generated by the crosslinking irradiation (and thus improve the long-term wear resistance), the irradiated acetabular cups can be treated with one or more of the following: pressurization in hydrogen, annealing, and treatment with ethylene oxide to reduce or eliminate the residual fee radicals.

The irradiated cup is annealed by heating it below the melting temperature of the non-crosslinked PE. As used in this patent application, the melting temperature is identified from the peak of the melting endotherm as measured by differential scanning calorimetry (DSC). The annealing temperature is preferably from about room temperature to below the melting temperature; more preferably from about 90° C. to about 10° C. below the melting temperature; and most preferably from about 80° C. to about 50° C. below the melting temperature. UHMWPE may be annealed at a temperature from about 25° C. to about 132° C., preferably from about 40° C. to about 120° C., and more preferably from about 50° C. to about 80° C. The annealing period is preferably from about 2 hours to about 7 days, and more preferably from about 7 hours to about 6 days, and most preferably from about 10 hours to about 5 days.

The irradiated implant may be treated with hydrogen to further reduce or eliminate free radicals. A hydrogen treatment method is illustrated in EXAMPLE 4, below. One skilled in the art, based on EXAMPLE 4, would be able by simple trial and error without undue experimentation to arrive at the appropriate parameters for eliminating or reducing the desired amount of free radicals by simple trial and error. Examples of minimum and maximum starting points for such trial and error would be pressurizing the cup in hydrogen to about 30 psi for about 18 hours, or to about 90 psi for about 72 hours, respectively.

Method 2: E-beam Irradiation Followed by Remelting or Annealing

In this method, instead of starting with an acetabular cup, a partially formed cup is used. This partially formed cup consists of the original bulk material (e.g., extruded bar or molded block) in which is shaped, e.g., by machining, the intended bearing surface of the cup. This bearing surface is then e-beam irradiated as in Method 1 (including at room temperature), above. The irradiated partially formed cup is then remelted or annealed, either in air or in a low oxygen atmosphere, to reduce free radicals and increase long term wear resistance. Remelting is a very effective and efficient method to reduce free radicals.

The remelting temperature is at or above the melting temperature of the maximum crosslinked region in the cup. Preferably, the remelting temperature is from about such melting temperature to about 100° C. to about 160° C. above the melting temperature; more preferably from about 40° C. to about 80° C. above the melting temperature; and most preferably from about 1° C. to about 60° C. above the melting temperature. For example, in the case of UHMWPE, the remelting temperature is preferably from about 134° C. to about 300° C., more preferably from about 134° C. to about 250° C., and most preferably from about 134° C. to about 200° C.

The annealing temperature is below the melting temperature of the maximum crosslinked region in the cup, preferably from about room temperature to below the melting temperature; more preferably from about 90° C. to about 1° C. below the melting temperature; and most preferably from about 60° C. to about 1° C. below the melting temperature. For example, UHMWPE may be annealed at a temperature from about 25° C. to about 132° C., preferably from about 50° C. to about 132° C., and more preferably from about 80° C. to about 130° C. The annealing period is preferably from about 2 hours to about 7 days, and more preferably from about 7 hours to about 5 days, and most preferably from about 10 hours to about 2 days.

The thermal treatment methods described in WO 98/01085 are also applicable to improve the resistance to oxidation and, thereby, the resistance to wear of the surface crosslinked PE of the present invention. WO 98/01085 is hereby incorporated by reference in its entirety.

After the remelting and annealing, the final shape of the cup is fashioned, e.g., by machining out of the partially formed cup. Any distortion /or oxidized layer of the PE caused by the remelting or annealing is thereby corrected or removed, respectively, in the process of the final shaping. In this case, the depth of the initial crosslinking would be increased, such that, after the final shaping, the remaining crosslinked layer would be of the desired thickness.

Method 3: E-beam Irradiation in the Melt

Method 3 is the same as Method 2, except that the partially formed cup is irradiated in the melt (at or above melting temperature of UHMWPE) instead of at room temperature.

Given the teaching in this patent application, one skilled in the art can arrive at his desired gradient-surface crosslinked PE and implant. For example, one skilled in the art can easily calculate the necessary dosage to achieve the desired penetration or crosslinking profile, and for polyethylene of a given density. As shown in EXAMPLE 1, one skilled in the art can, through preliminary calculations and/or straightforward trial-and-error, appropriately adjust the combination of the e-beam energy and the exposure time to obtain a desired maximum crosslinking in the surface layer and a rate of decrease below this layer, in order to get the required improvement in wear resistance in a surface layer of desired thickness.

(III) Chemical Crosslinking

Figure 2:
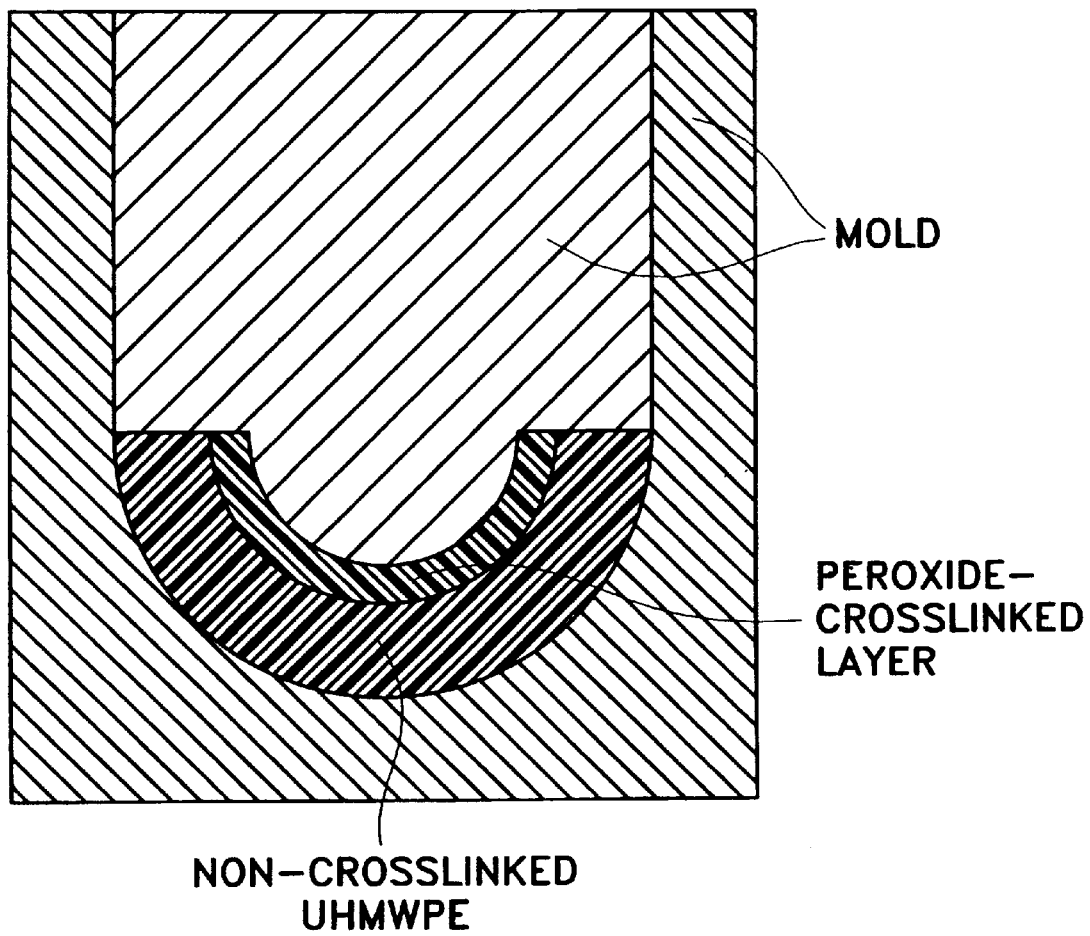
FIG. 2 schematically shows an UHMWPE acetabular cup in a cup mold, with a thin layer of UHMWPE powder that has been mixed with peroxide to form a thin crosslinked layer at the bearing surface, with uncrosslinked UHMWPE below this layer to preserve the original physical properties of the UHMWPE.

In another aspect of the invention, the bearing surface layer of the acetabular cup is chemically crosslinked, while leaving non-crosslinked UHMWPE below the chemically crosslinked surface layer. FIG. 2 schematically shows the structure of this acetabular cup. Although the drawing shows an abrupt boundary between the crosslinked surface layer and the non-crosslinked material, in practice this is preferably a gradual transition, which leaves the interior of the PE uncrosslinked (see e.g., FIG. 7). The following provides two non-limiting methods for achieving such surface-gradient crosslinked material.

Method A

PE powder is placed in an implant mold and then cold-pressed for a sufficient time to compact the powder, to a slight oversize of the I.D. to allow for the addition of a crosslinked layer. Next, additional PE powder is mixed with a free radical generating chemical. The term "free radical generating chemical" is hereinafter referred to as "FRGC". If the FRGC is a peroxide, it can be mixed with the PE powder while dry, or it can be dissolved in an inert solvent before being added to the PE powder. Examples of such inert solvents are alcohol and acetone. After the PE powder has been mixed with the inert solvent containing the peroxide, the inert solvent is then evaporated.

A thin layer of the PE powder with the FRGC is then placed on the area of the intended bearing surface on the previously compacted powder, and the combination is then further cold-pressed to compact both layers of powder. The compacted layers are then compression molded using standard methods known in the art for molding PE.

Method B

In this method, PE powder is placed in an implant mold and compression molded using methods known in the art to a slight oversize of the I.D. to allow for the addition of a crosslinked layer. A thin layer of PE powder mixed with FRGC is then placed over the intended bearing surface and cold-pressed to compact it, and then compression molded using methods known in the art, thereby simultaneously crosslinking the surface layer and fusing it to the bulk of the implant. Again, the FRGC can be a peroxide.

Alternatively, a PE implant can be preformed by machining in the usual manner, but to a slight oversize of the I.D., and then placed in a mold with the bearing surface coated with a layer of PE powder mixed with a FRGC, and then heat and pressure applied to crosslink the mixture and simultaneously fuse it to the preformed implant.

Thus, one skilled in the art can, by routine trial and error, modify the methods in EXAMPLE 2 to adjust the concentration of the FRGC used and/or the thickness of the layer of PE powder mixed with the FRGC applied and use the present invention in order to obtain a desired maximum level of crosslinking in the surface layer as well as a desired maximum depth of crosslinking.

i) Annealing of Chemically Crosslinked Implant

A chemically crosslinked implant may be annealed to shrink it to a stable size before shaping the cup into the final product. The annealed cup may be re-sized or shaped, such as by machining, into a product with the desired dimensions. The annealing temperature is preferably chosen to avoid thermal oxidation of the crosslinked PE and to minimize distortion of the cup. Thus, the annealing temperature is preferably below the melting point of the molded PE. For example, the melting temperatures of molded UHMWPE and molded 1 wt % peroxide crosslinked UHMWPE are about 132° C. and about 126° C. The preferable annealing temperature for both of these molded UHMWPE is between 60° C. to 125° C. and more preferably about 100° C. The annealing time is generally between 1 to 6 hours, and more preferably between 2 to 4 hours. In the case of UHMWPE, the annealing time is preferably between 2 to 4 hours, and more preferably about 2 hours. To further avoid thermal oxidation of the crosslinked PE, the annealing is most preferably conducted in a low oxygen environment, e.g., in a vacuum oven or in inert atmosphere.

ii) Soaking of a Peroxide Crosslinked Implant

For implants which are crosslinked by peroxide, after the crosslinking, residual chemicals may be removed from the crosslinked layer by soaking the implant, e.g., from 1 to 10 days, in suitable solvents, such as acetone or 95% alcohol. One skilled in the art may use the method described in EXAMPLE 3 to determine the length of time for soaking his particular PE or implant to achieve his desired decrease or elimination of the peroxide.

iii) Examples of FRGC

Conventional methods for chemical crosslinking of UHMWPE which can be modified to produce the present surface-gradient crosslinked UHMWPE and implants are described in e.g., de Boer, J. & Pennings, A. J., *Makromol. Chem. Rapid Commun.*, 2:749 (1981); de Boer, J. & Pennings, A. J., *Polymer*, 23:1944 (1982); de Boer, J., et al., *Polymer*, 25:513 (1984) and Narkis, M., et al., *J. Macromol. Sci. Phys.*, B 26:37, 58 (1987). The method described in EP 0722973 A1, above may also be modified to produce the present novel UHMWPE and implants. For example, the crosslinking chemical, FRGC, may be any chemical that decomposes at the molding temperature to form highly reactive intermediates, free radicals, which would react with the PE to form the crosslinked network. Examples of FRGC are peroxides, peresters, azo compounds, disulfides, dimethacrylates, tetrazenes, and divinyl benzene. Examples of azo compounds are: azobis-isobutyronitride, azobis-isobutyronitrile, and dimethylazodi isobutyrate. Examples of peresters are t-butyl peracetate and t-butyl perbenzoate.

Preferably the PE is crosslinked by treating it with an organic peroxide. The preferable peroxides are 2,5-dimethyl-2,5-bis(tert-butylperoxy)-3-hexyne (Lupersol 130, Atochem Inc., Philadelphia, Pa.); 2,5-dimethyl-2,5-di-(t-butylperoxy)-hexane; t-butyl alpha-cumyl peroxide; di-butyl peroxide; t-butyl hydroperoxide; benzoyl peroxide; dichlorobenzoyl peroxide; dicumyl peroxide; di-tertiary butyl peroxide; 2,5 dimethyl-2,5 di(peroxy benzoate) hexyne-3; 1,3-bis(t-butyl peroxy isopropyl) benzene; lauroyl peroxide; di-t-amyl peroxide; 1,1-di-(t-butylperoxy) cyclohexane; 2,2-di-(t-butylperoxy)butane; and 2,2-di-(t-amylperoxy) propane. The more preferred peroxide is 2,5-dimethyl-2,5-bis(tert-butylperoxy)-3-hexyne. The preferred peroxides have a half-life of between 2 minutes to 1 hour; and more preferably, the half-life is between 5 minutes to 50 minutes at the molding temperature. The preferred peroxide concentration is from 0.2 weight percent (wt %) to 2 wt %; preferably from 0.2 wt % to 1 wt %; and more preferably from 0.4 wt % to 1.0 wt %. The peroxide can be dissolved in an inert solvent before being added to the polymer powder. The inert solvent preferably evaporates before the polymer is molded. Examples of such inert solvents are alcohol and acetone.

(IV) Sterilization

The implants of the present invention may be sterilized using methods known in the art, such as by ethylene oxide, gas plasma or gamma irradiation sterilization. Ethylene oxide sterilization has the additional benefit of decreasing oxidation susceptibility of electron irradiated PE (and, thus, increasing the long term wear resistance, see e.g., EXAMPLE 4, below) by reducing any residual free radicals resulting from e-beam radiation.

The invention may be better understood with reference to the accompanying examples, which are intended for purposes of illustration only and should not be construed as in any sense as limiting the scope of the invention as defined in the claims appended hereto.

EXAMPLES

Example 1

SURFACE CROSSLINKING WITH LOW ENERGY E-BEAM IRRADIATION

Materials

Commercial-grade UHMWPE extruded bars (GUR 1050, 3" diameter, Poly Hi Solidur, Ft Wayne, Ind.), with a weight average molecular weight of from $5 \times 10^6$ to $6 \times 10^6$ gram per mole, were used as received. The 8 mm thick disk specimens were cut from the bars and irradiated with an e-beam at room temperature in nitrogen atmosphere at Radiation Dynamics, Inc. (New York, N.Y.) to doses ranging from 5 to 15 Mrad. To produce materials with surface crosslinking but with the interior uncrosslinked, one set of specimens was irradiated at 0.875 MeV at a dose rate of 1.35 Mrad/sec, producing a surface dose of 5 Mrad that dropped to 2.5 Mrad at a depth of about 2 mm and to nearly zero at about 2.5 mm (FIG. 3), another set of specimens was irradiated at 0.650 MeV at a dose rate of 1.35 Mrad/sec to obtain a surface dose of 10 Mrad, decreasing to about 5 Mrad at a depth of 1 mm and to nearly zero at about 1.5 mm, and the third set of specimens was irradiated at 650 kV at a dose rate of 1.35 Mrad/sec to obtain a surface dose of 15 Mrad, decreasing to about 7.5 Mrad at a depth of 1 mm and to nearly zero at about 1.5 mm deep. After irradiation, the specimens were stored in nitrogen atmosphere. The physical properties of the irradiated specimens were characterized by differential scanning calorimetry (DSC) and by gel content analysis (to indicate the extent of crosslinking).

DSC

For DSC measurements, a core about 5 mm dia. was cut from the sample and the core was microtomed into 200 $\mu$m thick sections across the depth. Specimens weighing about 4 mg were heated from 50° C. at 10° C./min in a differential scanning calorimeter (Perkin-Elmer DSC-4) to 170° C. The melting temperature was identified from the peak of the melting endotherm. Indium was used for calibration of the temperature.

Gel Content Analysis

The gel content of each material was analyzed as a function of depth from the crosslinked surface. 100 $\mu$m thick sections (about 30–50 mg each) were microtomed across the specimen. Extraction of the sol-fraction was performed by boiling in p-xylene for 24 hours, with 0.5 wt % of antioxidant (2,6-di-t-butyl-4-methyl phenol) added to prevent oxidation. For lightly crosslinked sections below the highly crosslinked surface, the specimens were wrapped in PTFE (Teflon) membrane filter (0.5 $\mu$m pore size) to avoid loss of gel. After extraction, the specimens were deswollen in acetone and dried at 60° C. in a vacuum oven to constant weight. The gel fraction was determined from the ratio of the weight of the dried-extracted material to that of the dry non-extracted material.

Results and Discussion

Figure 3:
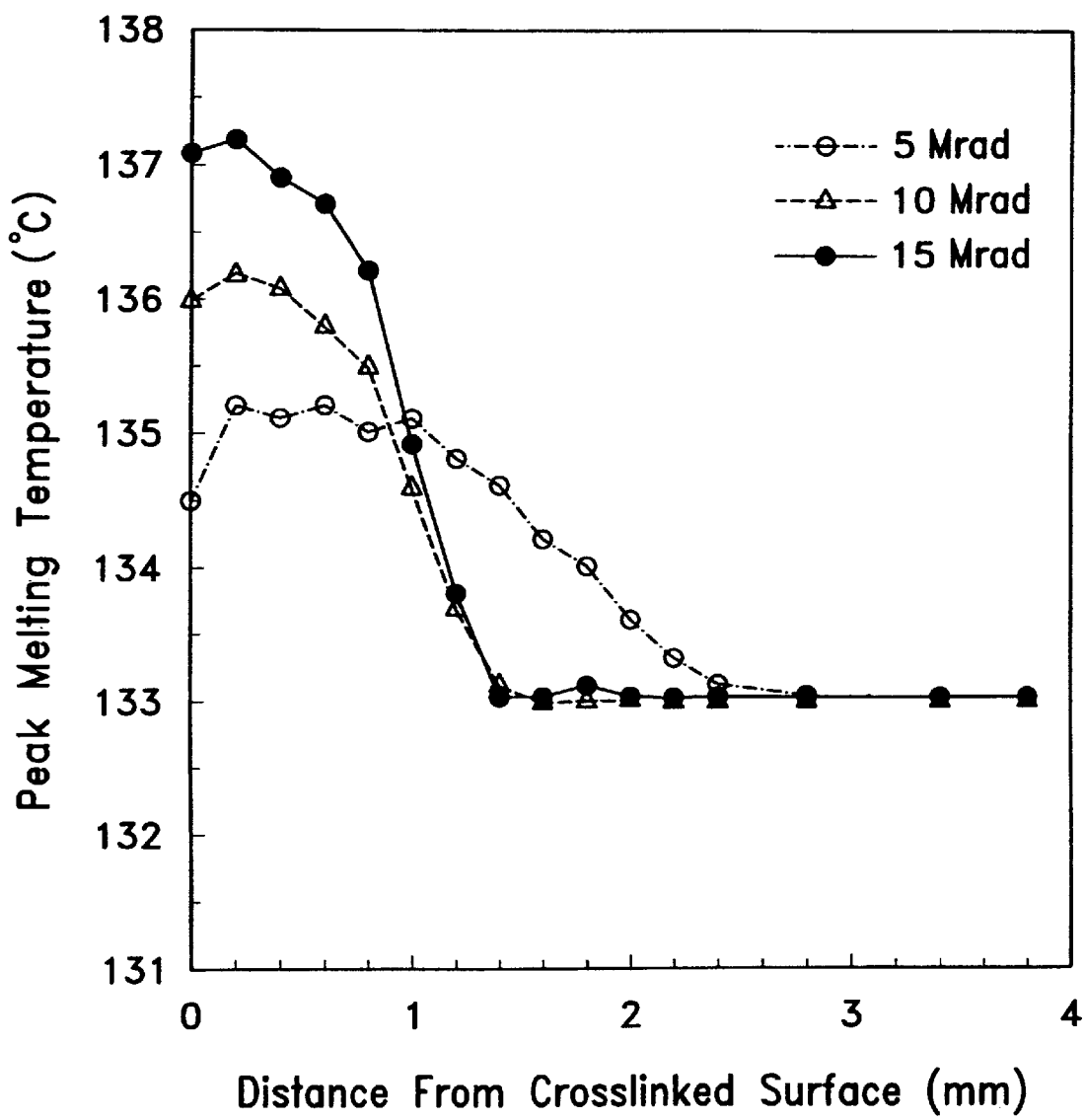
FIG. 3 graphically presents the peak melting temperature vs distance from the e-beam crosslinked surface of UHMWPE specimens.

As shown in FIG. 3, e-beam irradiation increased the melting temperature of the crosslinked surface layer of the 8 mm thick UHMWPE specimens. There was a strong gradient in melting temperature for all irradiated specimens. The melting temperature decreased gradually with depth and, eventually, there was no temperature increase in the interior, indicating that no crosslinking had occurred. The crosslinking depth depended on the energy of the e-beam. The dose at a given depth depended on the exposure time. For example, the crosslinking depth extended to about 3 mm deep with the 0.875 MeV beam (5 Mrad specimens) and about 1.8 mm deep with the 0.650 MeV beam (10 and 15 Mrad specimens). There was a greater increase in melting temperature with increasing radiation dosage (FIG. 3). The gel content (i.e., the extent of crosslinking, FIG. 4) also increased with increasing radiation dosage, with the maximal gel contents being about 93, 95 and 96% for 5, 10 and 15 Mrad specimens, respectively.

Example 2

SURFACE CHEMICALLY-CROSSLINKED UHMWPE MADE WITH PEROXIDE

Materials

Commercial-grade UHMWPE flake (GUR 1050, Poly Hi Solidur), with a weight average molecular weight of from $5 \times 10^6$ to $6 \times 10^6$ gram per mole, was used as received. The peroxide was 2,5-dimethyl-2,5-bis(tert-butylperoxy)-3-hexyne (Lupersol 130, Atochem Inc., Philadelphia). Mixing of the UHMWPE and the peroxide was accomplished by dispersing UHMWPE powder in an acetone solution of the peroxide and subsequently evaporating the acetone (using the method described in EP 0722973 A1, "Chemically Crosslinked Ultrahigh Molecular Weight Polyethylene for Artificial Human Joints" of R. Salovey, et al.). The surface crosslinked UHMWPE specimens were synthesized according to the following procedures:

Method A

The original UHMWPE powder was placed in a rectangular mold (dimension 8.8×3.7×2.8 cm) and then cold-pressed at room temperature and 2000 psi pressure on the powder for 10 minutes. A layer of UHMWPE powder mixed with either 1 wt % or 0.2 wt % peroxide (the layer was about 0.5 mm for 1 wt % peroxide; and about 1.0 mm for 0.2 wt % peroxide) was then placed on the compacted powder and the combination was then further cold-pressed at room temperature and 2000 psi pressure for 10 minutes. The compacted mixture was then heated to 170° C. under a 1000 psi pressure on the powder for 2 hours, and then slow-cooled to room temperature while held at 2000 psi pressure.

Method B:

The original UHMWPE powder was placed in the rectangular mold, heated to 170° C. under 1000 psi pressure on the powder for 1 hour and subsequently slow-cooled at 2000 psi pressure to below 100° C. A layer about 0.5 mm thick of UHMWPE powder mixed with 1 wt % peroxide was then placed on the top of the molded block and the block was cold-pressed at 2000 psi pressure for 10 minutes, heated to 170° C. for 2 hours at 1000 psi pressure, and then slow-cooled to room temperature while held at 2000 psi pressure. The physical properties of the specimens surface crosslinked by Methods A or B were characterized by DSC and gel content analysis, as described in EXAMPLE 1.

Results and Discussion

Figure 5:
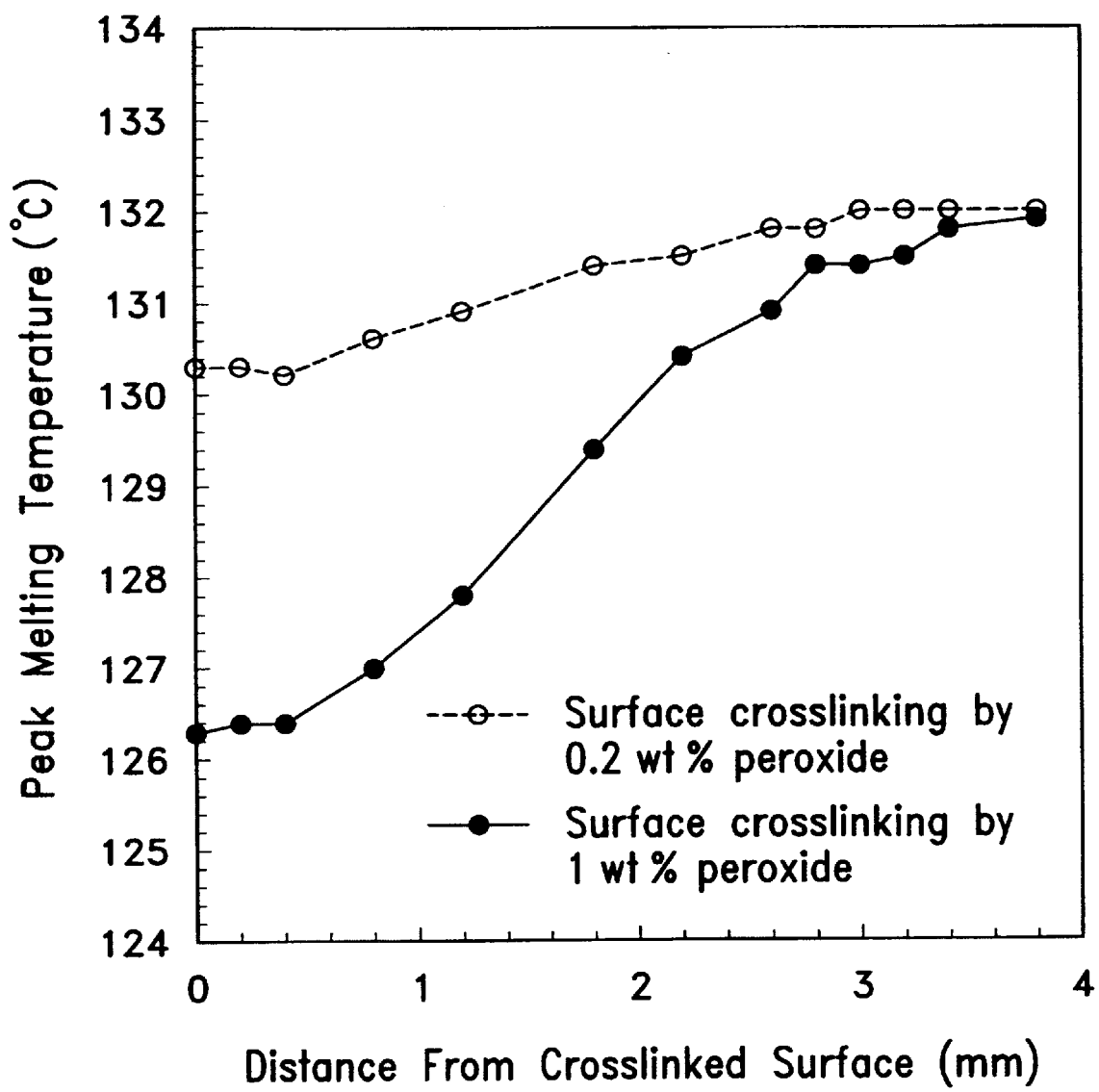
FIG. 5 graphically presents the peak melting temperature vs distance from the peroxide crosslinked surface of UHMWPE specimens.
Figure 6:
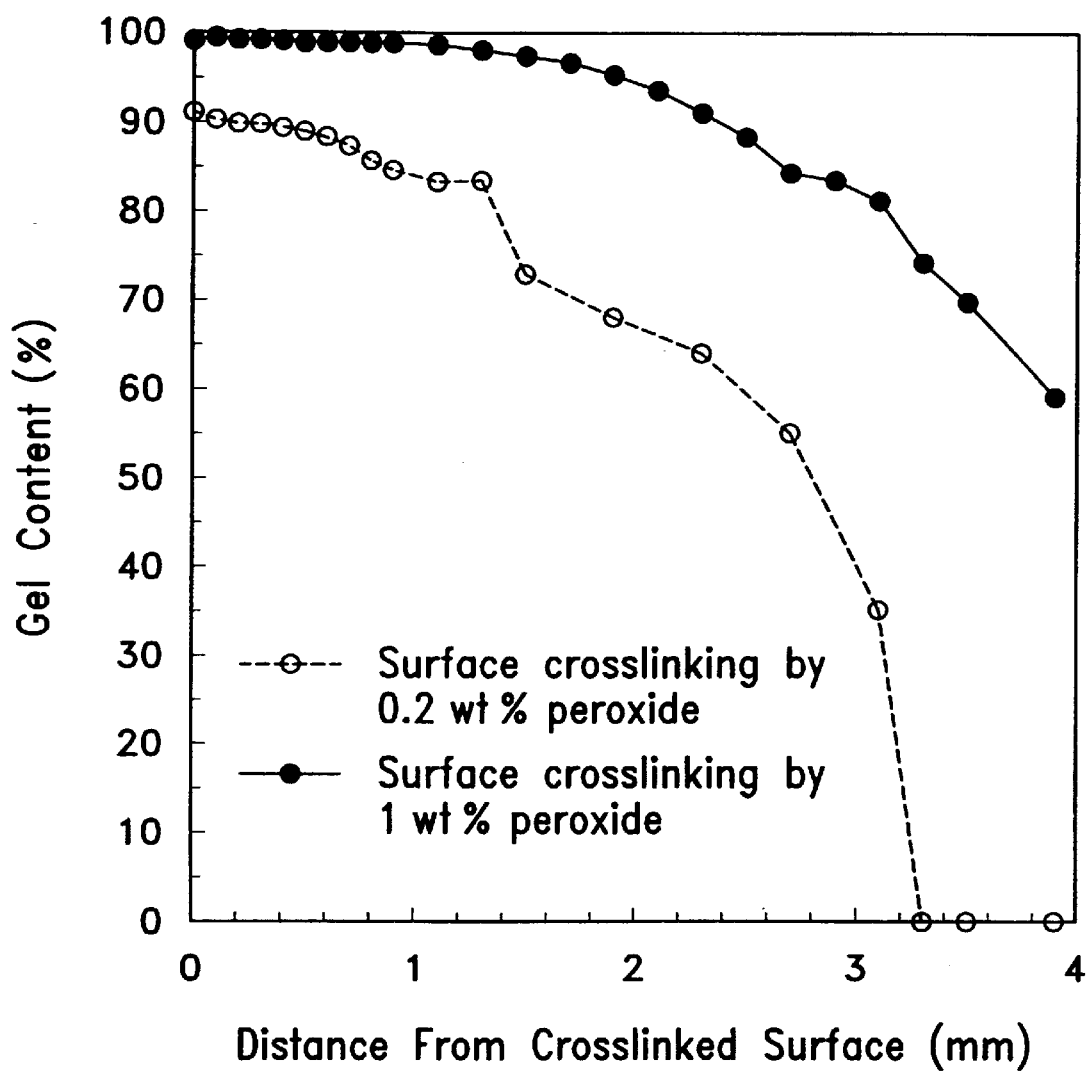
FIG. 6 graphically presents the gel content vs distance from the peroxide crosslinked surface of UHMWPE specimens.

The melting temperatures and gel content profiles of the surface crosslinked UHMWPE produced with Method A are shown in FIGS. 5–6, respectively. Unlike radiation crosslinked specimens (FIG. 3), for which the melting temperature was increased by crosslinking, with peroxide crosslinking during molding, the melting temperature of the specimens decreased after crosslinking, due to the specimens recrystallizing in a crosslinked melt. The more the peroxide, the lower the melting temperature (FIG. 5). There was a strong gradient in melting temperature for specimens crosslinked with both 0.2 and 1 wt % peroxide. The interpenetration of the peroxide-mixed and non-mixed UHMWPE and the diffusion of peroxide during molding resulted in the crosslinked layer penetrating about 4 mm into the PE. With 1 wt % peroxide crosslinking, the surface layer (about 1 mm thick) exhibited almost a 100% gel content (FIG. 6), gradually decreasing to about 60% at about 4 mm deep. In contrast, with 0.2 wt % peroxide crosslinking, the gel content was about 90% in the surface layer, decreasing more rapidly with depth and becoming effectively zero at a depth of about 3.3 mm.

Figure 7:
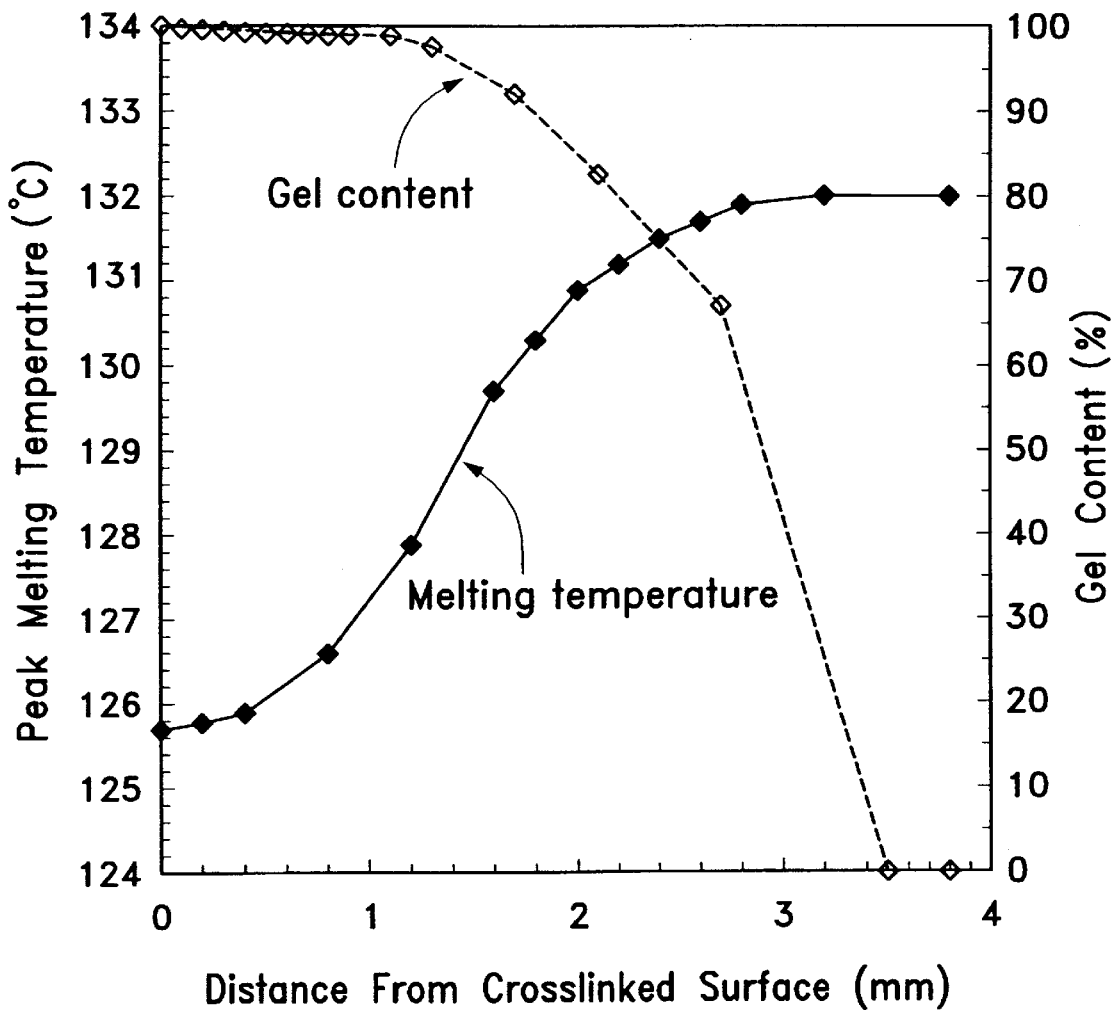
FIG. 7 graphically presents the melting temperature and gel content profiles of the peroxide crosslinked surface of UHMWPE specimens.

The melting temperature and gel content profiles of the UHMWPE surface crosslinked specimens using method B are shown in FIG. 7. Compared to the 1 wt % peroxide crosslinked specimen made with method A, the specimen made with method B exhibited steeper gradients in both the peak melting temperature and gel content (i.e., comparing FIG. 7 to FIGS. 5 and 6).

Example 3

EXTRACTION OF RESIDUAL CHEMICALS RESULTING FROM PEROXIDE DECOMPOSITION

Materials

Commercial-grade GUR 4150 UHMWPE original flake (Hoechst, Tex.), with a weight-average molecular weight of about from $5 \times 10^6$ to $6 \times 10^6$ gram per mole was used as received. Mixing of 1 wt % peroxide with the UHMWPE was as described in EXAMPLE 2, and crosslinked blocks, 8 mm thick, were prepared by heating the mixed powder at 170° C. and 1000 psi pressure on the powder for 2 hours. After 2 hours, the pressure on the specimen was increased to 2000 psi and the specimen was slowly cooled in the press to room temperature. Rather than surface crosslinking, as in EXAMPLE 2, these specimens were crosslinked throughout the entire thickness in order to determine the depth of extraction of the solvents.

Specimens to be extracted were soaked in ethanol or acetone at room temperature for 7 days and then dried in a vacuum oven at 50° C. overnight. The concentration of residual chemicals, as indicated by the tertiary alcohols, was examined using Fourier transform infrared spectrometry (FTIR).

FTIR

FTIR measurements were performed on the extracted and non-extracted specimens. Segments about 5 mm wide were cut from each PE specimen and then microtomed into 200 $\mu$m thick slices. The tertiary alcohol profiles were measured using a Mattson Polaris spectrophotometer (Model IR 10410) with a Spectra-Tech IR plan microscope. Spectra were collected in 100 $\mu$m steps through the entire specimen, using 64 scans summation at a resolution 16 $cm^{-1}$ with a MCT (Mercury Cadmium Telluride) detector. The tertiary alcohol concentration was indicated by the ratio of the peak height of the absorption band at 1173 $cm^{-1}$ to the height of the reference band at 2022 $cm^{-1}$ (i.e., representing the —$CH_2$— vibration).

Results and Discussion

Figure 8:
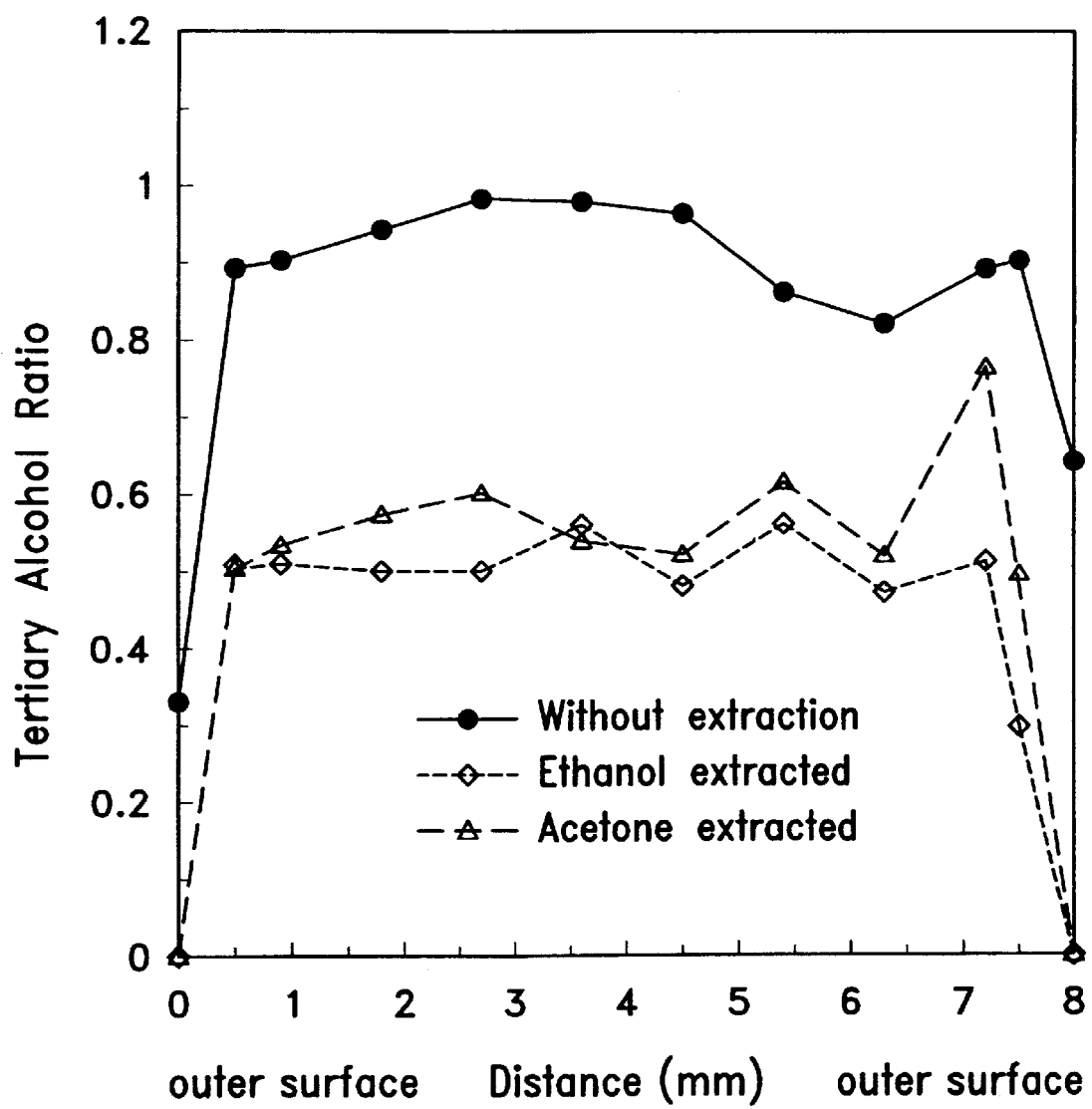
FIG. 8 graphically presents the extraction of tertiary alcohol from 1 wt % peroxide crosslinked UHMWPE specimens.

As shown in FIG. 8, extraction with ethanol or acetone reduced the tertiary alcohols to zero at the surface, with the concentration of tertiary alcohols increasing to about 40 to 50% of that of the non-extracted specimens at a depth of about 0.5 mm. Thus, one additional benefit of limiting the chemical crosslinking only to a surface layer is that the tertiary alcohols will primarily be present in the surface layer and, thus, more readily extracted with soaking in a solvent. Longer soak times would result in deeper extraction.

Example 4

THERMAL AGING OF UHMWPE THAT HAS BEEN SURFACE CROSSLINKED WITH E-BEAM IRRADIATION

Materials

The materials and irradiation methods were as described in EXAMPLE 1. The 8 mm thick UHMWPE specimens were surface-crosslinked with e-beam irradiation to 5, 10 or 15 Mrad while in a nitrogen atmosphere. After irradiation, specimens from each radiation dosage were subject to the following treatments: (1) stored in pressurized hydrogen atmosphere at 30 psi and room temperature for 18 hours; (2) sterilized with ethylene oxide after hydrogen treatment, using regular sterilization procedures; or (3) sterilized with ethylene oxide without hydrogen treatment. One set of specimens from each radiation dose was used as controls, i.e., without any post-irradiation treatments.

To examine the oxidation resistance of the irradiated specimens with or without post-irradiation treatments, the above specimens were heated in an oven slowly (at about 0.2° C./min) to 80° C. at ambient atmosphere and held at 80° C. for 11 days. After this thermal aging, the extent of oxidation of the aged specimens was examined with FTIR as a function of depth.

FTIR

Segments about 5 mm wide were cut from each PE specimen and then microtomed into 200 μm thick slices. The oxidation profiles, as indicated by the carbonyl concentration, were measured using a Mattson Polaris FTIR spectrophotometer (Model IR 10410) with a Spectra-Tech IR plan microscope. Spectra were collected in 100 μm steps from the surface to the middle of the specimen, using 64 scans summation at a resolution 16 cm$^{-1}$ with a MCT (Mercury Cadmium Telluride) detector. The carbonyl group concentration was indicated by the ratio of the peak height of the ketone absorption band at 1717 cm$^{-1}$ to the height of the reference band at 2022 cm$^{-1}$ (—$CH_2$— vibration).

Results and Discussion

Figure 9:
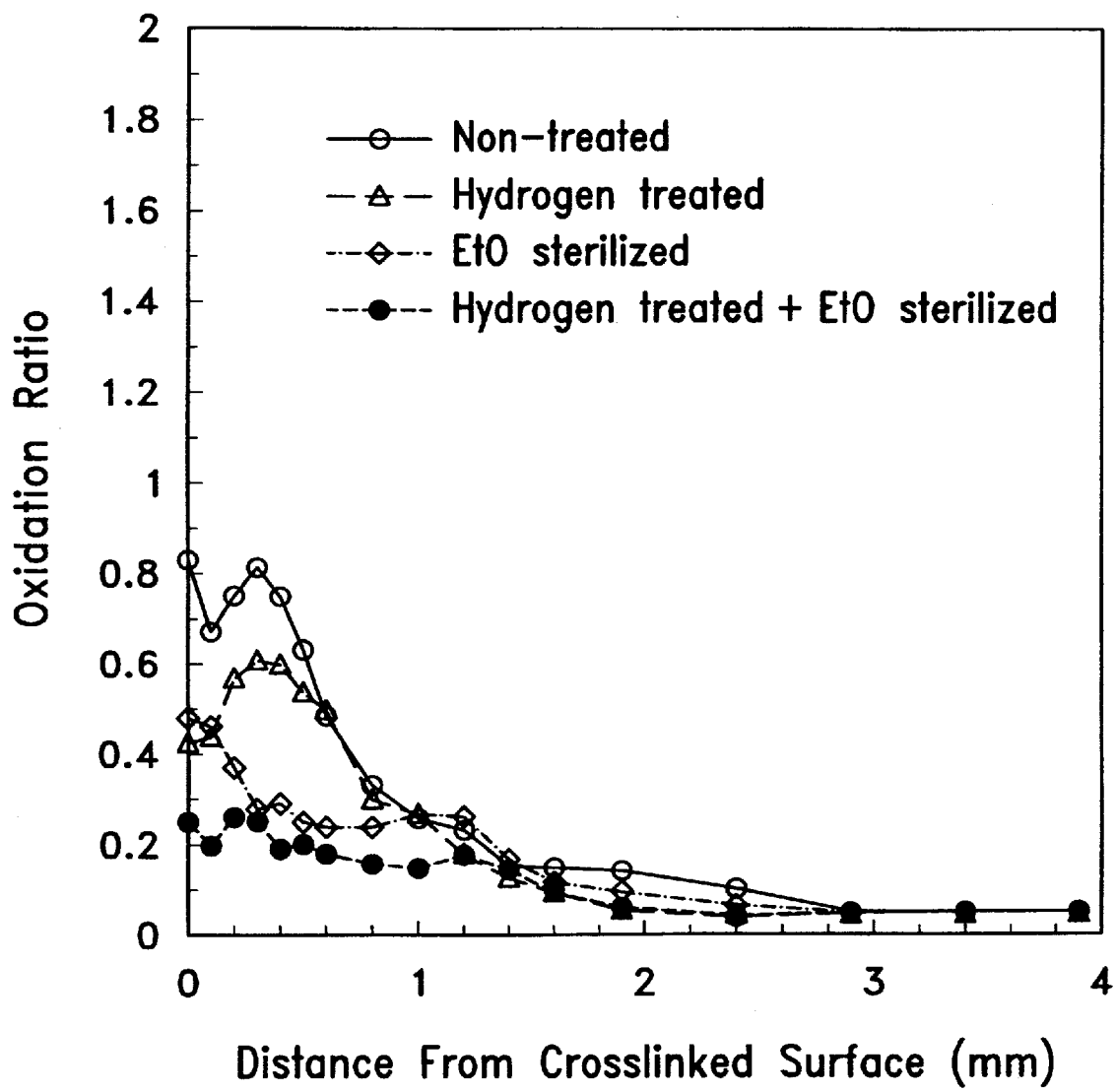
FIG. 9 graphically presents the oxidation depth profiles of aged e-beam (at 5 Mrad) crosslinked UHMWPE specimens with or without hydrogen and/or ethylene oxide treatments.
Figure 10:
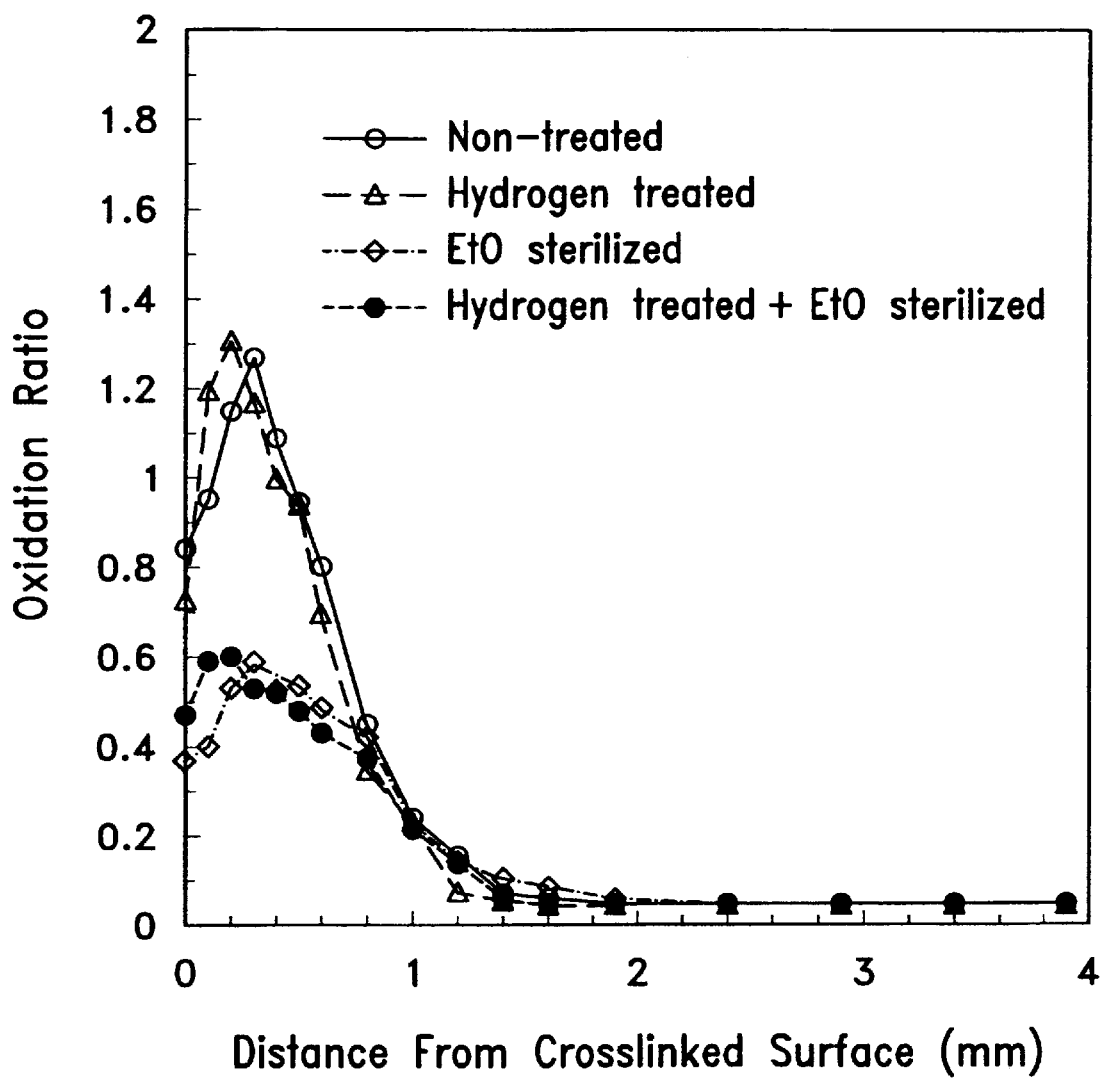
FIG. 10 graphically presents the oxidation depth profiles of aged e-beam (at 10 Mrad) crosslinked UHMWPE specimens with or without hydrogen and/or ethylene oxide treatments.
Figure 11:
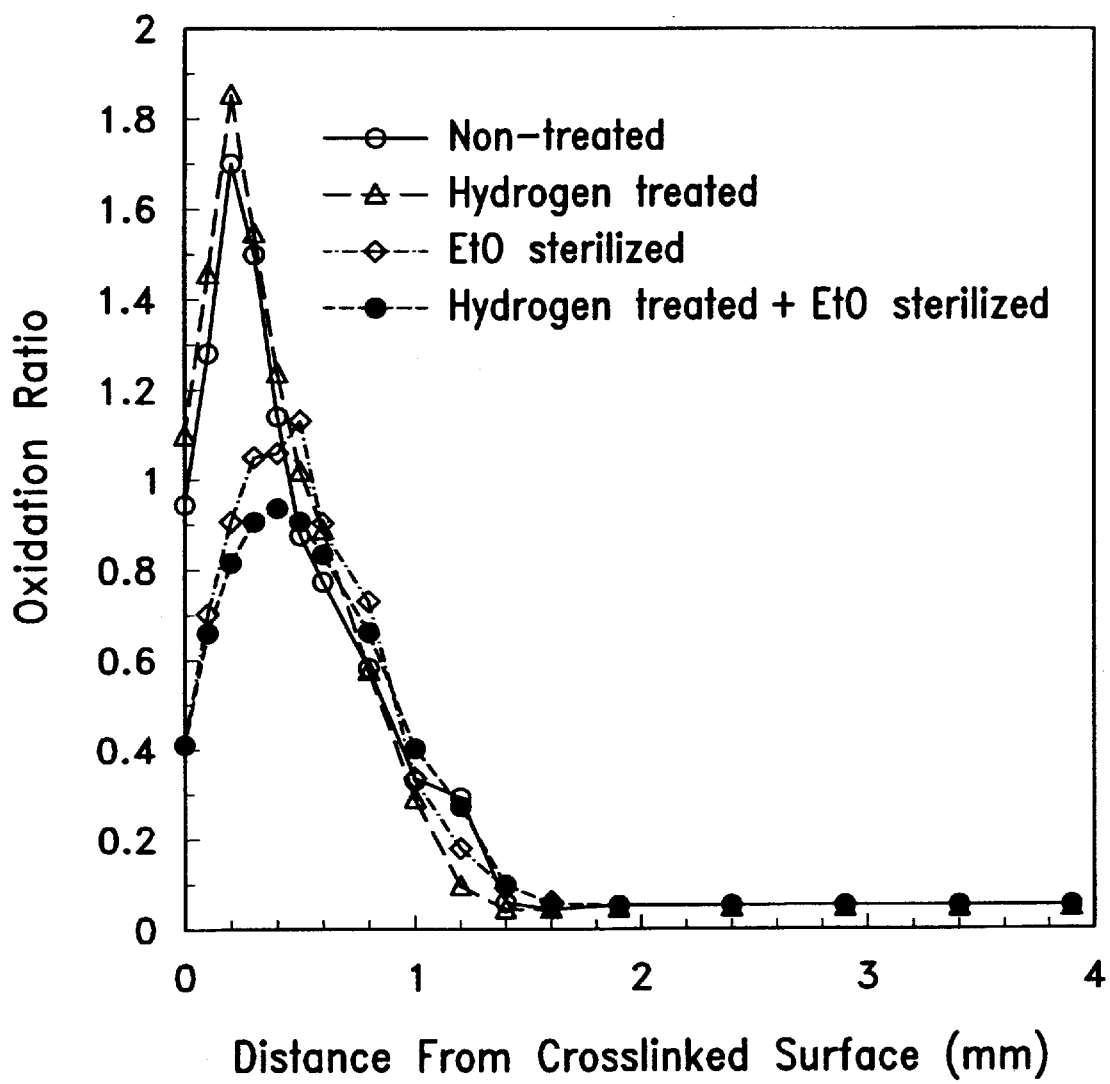
FIG. 11 graphically presents the oxidation depth profiles of aged e-beam (at 15 Mrad) crosslinked UHMWPE specimens with or without hydrogen and/or ethylene oxide treatments.

The oxidation profiles as a function of depth are shown in FIGS. 9 to 11. As shown in FIG. 9 for the 5 Mrad materials, hydrogen treatment or ethylene oxide sterilization apparently reduced the susceptibility of the material to oxidation, compared to the non-treated material, as indicated by the low oxidation ratio. The material treated with hydrogen and then sterilized with ethylene oxide exhibited the least oxidation, i.e., about 70% lower near the surface than in the non-treated material, indicating that both hydrogen treatment and/or ethylene oxide sterilization effectively reduce the residual free radicals resulting from e-beam irradiation.

After thermal aging, the oxidation was greater for higher radiation dosage (FIGS. 9 to 11). For the 10 Mrad materials (FIG. 10), ethylene oxide sterilization alone, or hydrogen treatment followed by ethylene oxide sterilization substantially reduced the residual free radicals, resulting in much lower oxidation, but there was little effect of hydrogen treatment alone, and there was little difference between the ethylene oxide specimens with or without hydrogen treatment. Similar results were obtained for the 15 Mrad materials (FIG. 11).

Although the hydrogen treatment of the time and pressures used in the present example had a marked effect only for the lower dose (5 Mrad) specimens, the effectiveness for the higher doses could be increased by increasing the time and/or pressure of exposure while at either room temperature or elevated temperature, thereby improving the resistance of the crosslinked surface layer to long-term oxidation. One skilled in the art can adjust these conditions, using routine trial and error, to decrease the long-term oxidation.

Example 5

SURFACE CROSSLINKED ACETABULAR CUP USING LOW-ENERGY ELECTRON BEAM IRRADIATION

Materials

Figure 12:
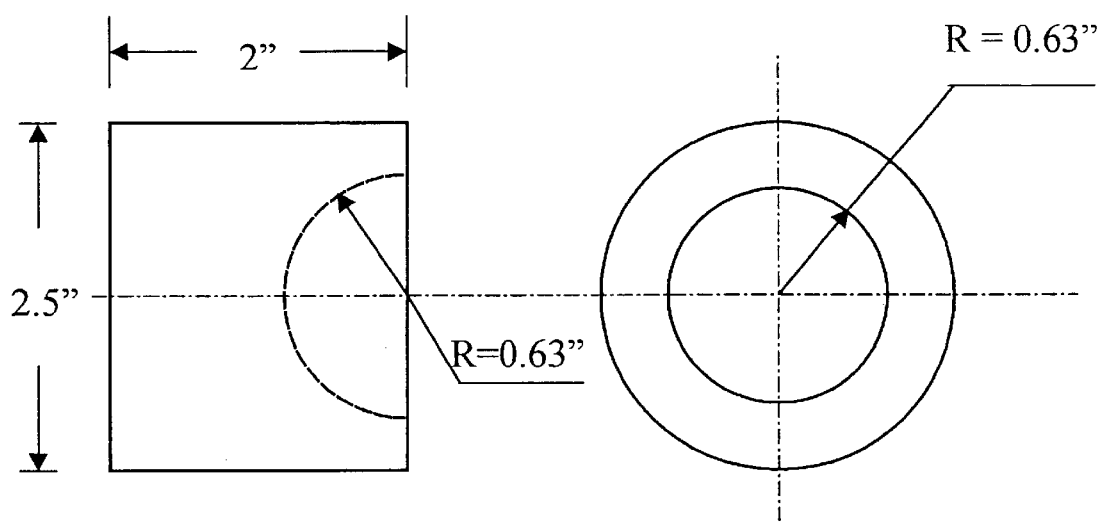
FIG. 12 schematically presents a partially formed acetabular cup.

Commercial-grade extruded bars of UHMW polyethylene (GUR 1050, Poly Hi Solidur, Ft Wayne, Ind.), with a weight average molecular weight of 5 to 6×10$^6$, were used as received. A partially formed acetabular cup with 1.26" I.D. (FIG. 12) was machined from the bar and irradiated with an electron beam at room temperature in a nitrogen atmosphere at Radiation Dynamics, Inc. (New York), in order to produce acetabular cups with crosslinking of the bearing surface, but with the interior uncrosslinked. One set of three specimens was placed flat on a stationary table (FIG. 13A) and then irradiated at 650 keV at a dose rate of 1.35 Mrad/sec, to produce a surface dose of approximately 10 Mrad but dropping to 5 Mrad at a depth of about 1 mm, and to nearly zero at about 2 mm. To provide more uniform crosslinking around the interior of the cup, a second set of three specimens was mounted on a rotary motor tilted at an angle of 45 degrees to the incident e-beam (FIG. 13B), such that the cups rotated during exposure and were irradiated to a surface dose of approximately 10 Mrad, as described above. After irradiation, the specimens were stored in a nitrogen atmosphere. In order to reduce the residual radicals produced by the irradiation, thereby improving the long-term resistance to oxidation, some of the specimens (taken from the set irradiated at 45 degrees) were then annealed in a vacuum oven at either 80° C. or 100° C. for 3 days, which applicants have found to improve the resistance to oxidative degradation (data not shown).

In order to assess the amount of crosslinking as a function of depth, as well as the distribution of the crosslinking around the interior of the cups, core samples were cut from: (a) the bottom center of the cups, (b) at 45 degrees from the bottom center, and (c) near the rim of the cup, and were microtomed to 200 micron thick sections. The thermal properties of the sections were characterized by (DSC), as described in EXAMPLE 1. The degree of oxidation as a function of depth was assessed using FTIR on microtomed cross-sections of the cups, as described in EXAMPLE 4.

Results and Discussion

Figure 14:
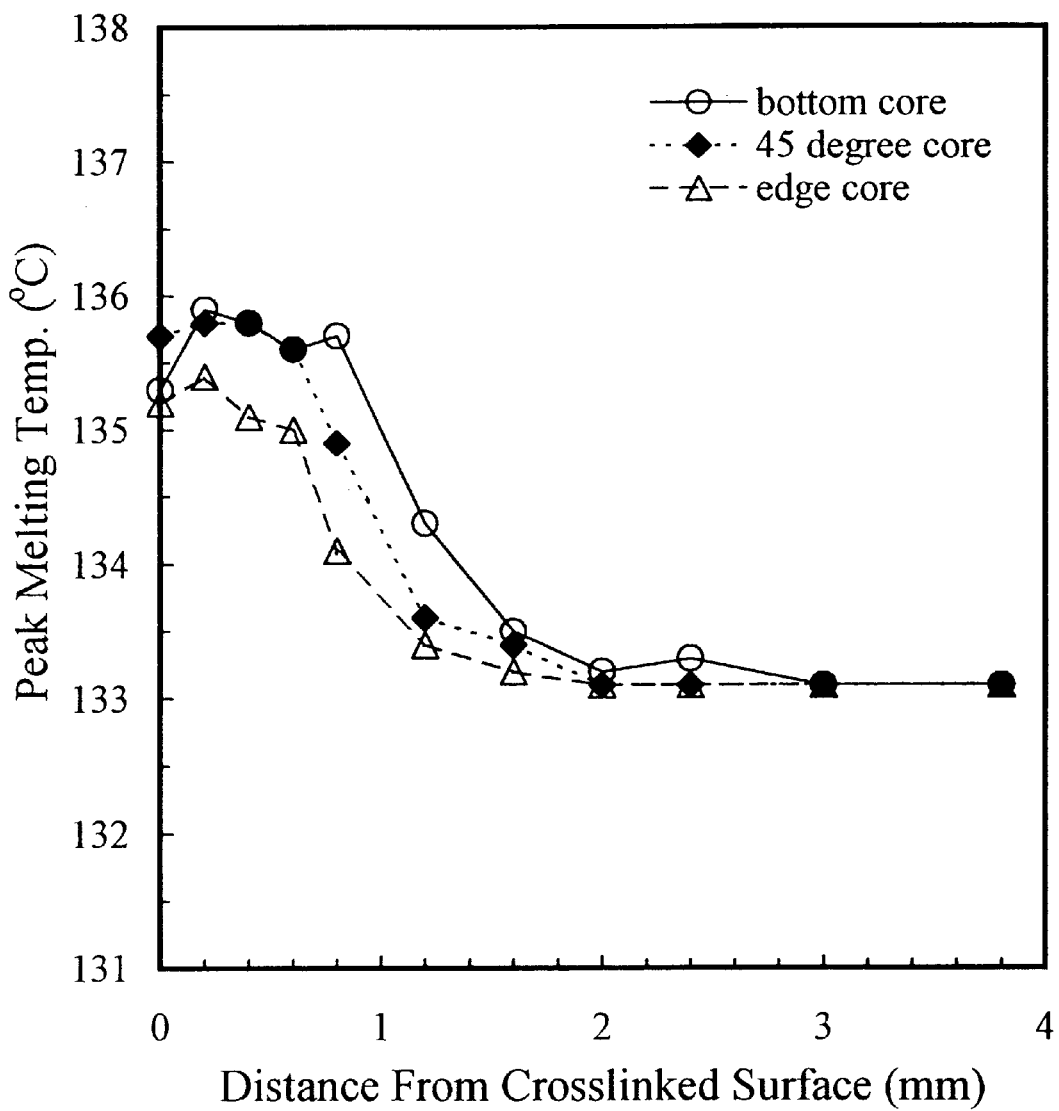
FIG. 14 graphically presents the profile of peak melting temperature versus distance from the surface of a surface-crosslinked partially formed cup irradiated to 10 MRad while the cup was placed on a stationary flat surface.

As shown in FIG. 14 for a cup that was irradiated while placed flat, the low-energy electron beam irradiation induced maximum crosslinking in the surface layer, as indicated by the increased melting temperature, that dropped to nearly zero crosslinking by about 2 mm deep, and the amount and depth of crosslinking was only slightly lower near the rim of the cup than at 45 degrees and near the bottom center.

Figure 15:
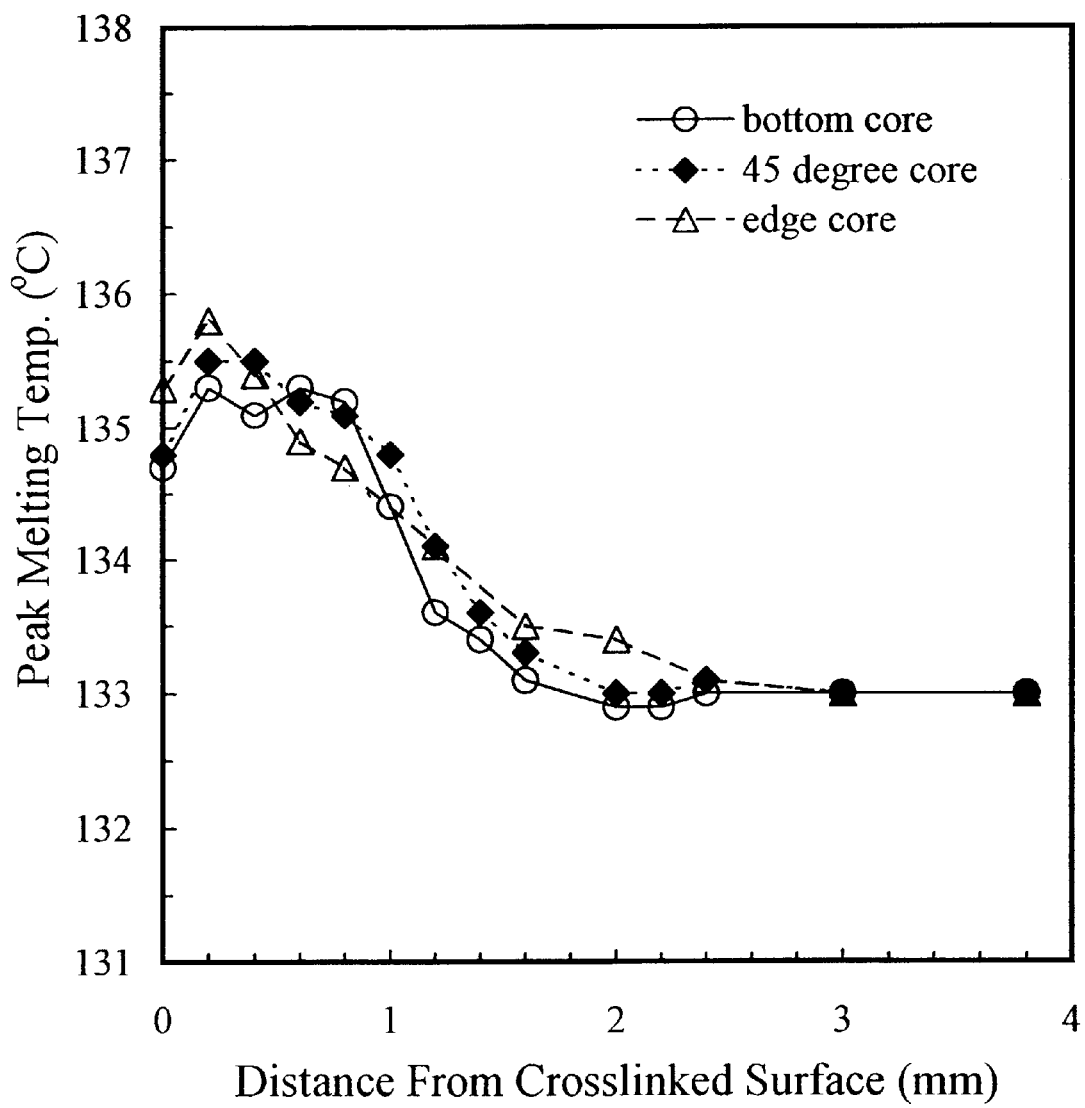
FIG. 15 graphically presents the profile of peak melting temperature versus distance from the surface of a surface-crosslinked partially formed cup irradiated with the e-beam at a 45 degrees to the central axis of the cup, to 10 Mrad on the cup surface and to 5 Mrad at 1 mm from the cup surface.

As shown in FIG. 15, irradiating the cup with the electron beam at 45 degrees (FIG. 13) and rotating the cup during exposure produced a slightly more uniform distribution of the amount and depth of crosslinking than was obtained when the cup was irradiated while simply placed flat on a stationary table (FIG. 14).

Figure 16:
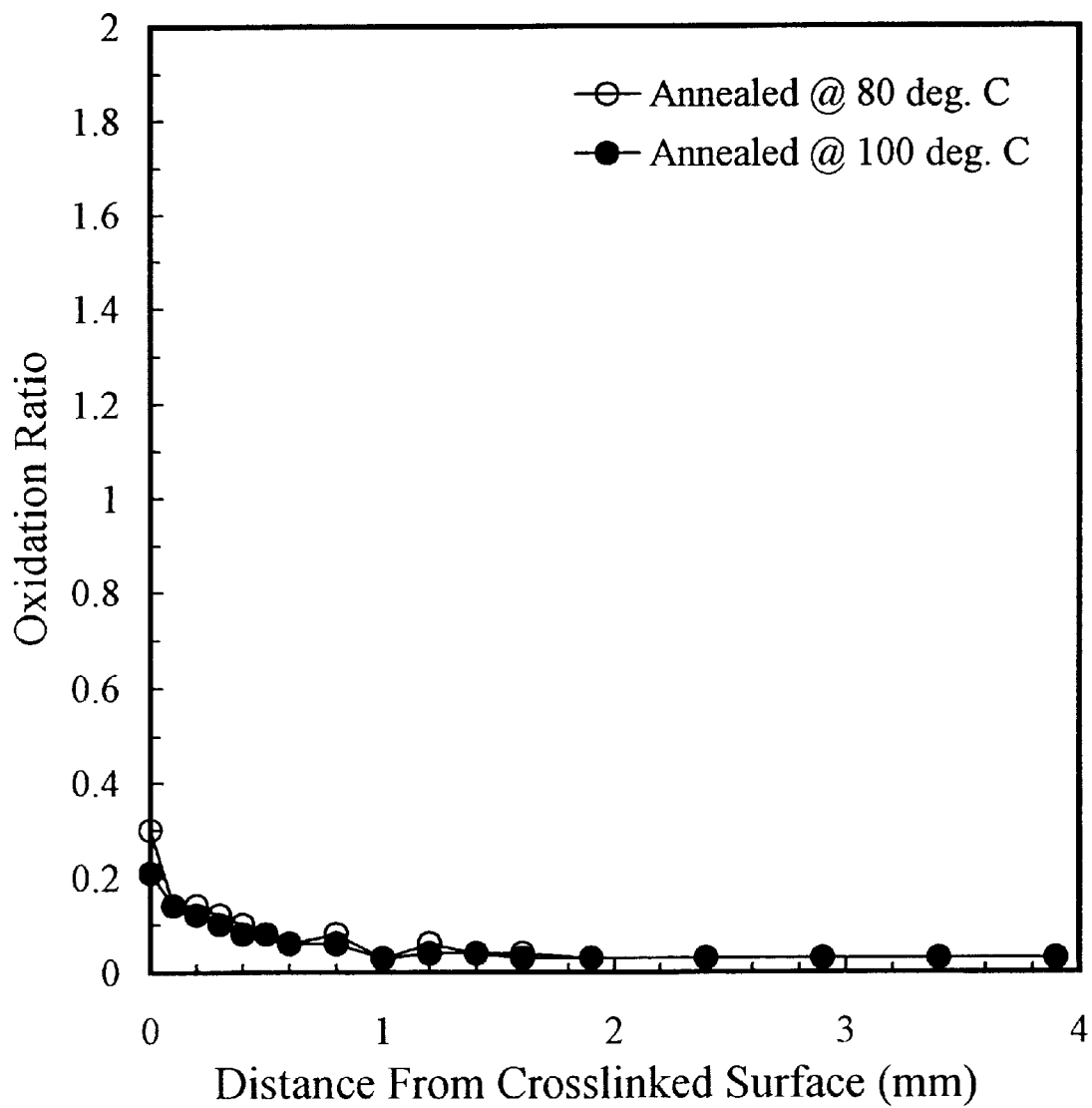
FIG. 16 graphically presents the profiles of oxidation versus distance from the surface of a surface-crosslinked partially formed cup after e-beam irradiation to 10 Mrad in the surface layer, and after annealing in vacuum at various temperatures for 3 days.

Even after annealing, there was only minor oxidation at the surface (FIG. 16). Thus, the final shape of acetabular cup can be machined out of the irradiated-annealed partially formed cup simply by shaping the outer surface. Nevertheless, if the minor oxidation at the surface is a concern, the partially formed cups can be made slightly undersized (i.e., slightly smaller I.D. than needed for the final product) prior to irradiation, and the lightly oxidized layer can be removed during the final machining, thereby producing maximal crosslinking at the initial bearing surface.

Example 6

SURFACE CHEMICALLY-CROSSLINKED UHMWPE ACETABULAR CUPS MADE WITH PEROXIDE CROSSLINKING

Materials

Commercial-grade UHMWPE flake (GUR 1050, Poly Hi Solidur), with a weight average molecular weight of 5 to 6×10$^6$, was used as received. The peroxide was 2,5- dimethyl-2,5 -bis(tert-butylperoxy)-3-hexyne (Lupersol 130, Atochem Inc.). Mixing of the UHMWPE and the peroxide was as described in EXAMPLE 2. Surface-crosslinked UHMWPE acetabular cups (32 mm I.D.) were fabricated according to the following procedure: the original UHMWPE powder was placed in the mold in the shape of an acetabular cup, heated to 170° C. under 1000 psi pressure on the powder for 1 hour, and subsequently slow-cooled at 2000 psi pressure to below 100° C. A layer of UHMWPE powder mixed with peroxide was then placed over the concave surface of the molded cup, the cup was cold-pressed at 2000 psi pressure for 10 minutes, heated to 170° C. for 2 hours at 1000 psi pressure, and then slow-cooled to room temperature while held at 2000 psi pressure.

To assess the depth of crosslinking into the bearing surface, cylindrical cores 5 mm in diameter were machined out of the bottom center of the cup and at 45° from the bottom center, and the cores were microtomed into sections each 200 micron thick. The melting temperature as a function of depth was then characterized by DSC, as described in EXAMPLE 1.

Results and Discussion

Figure 17:
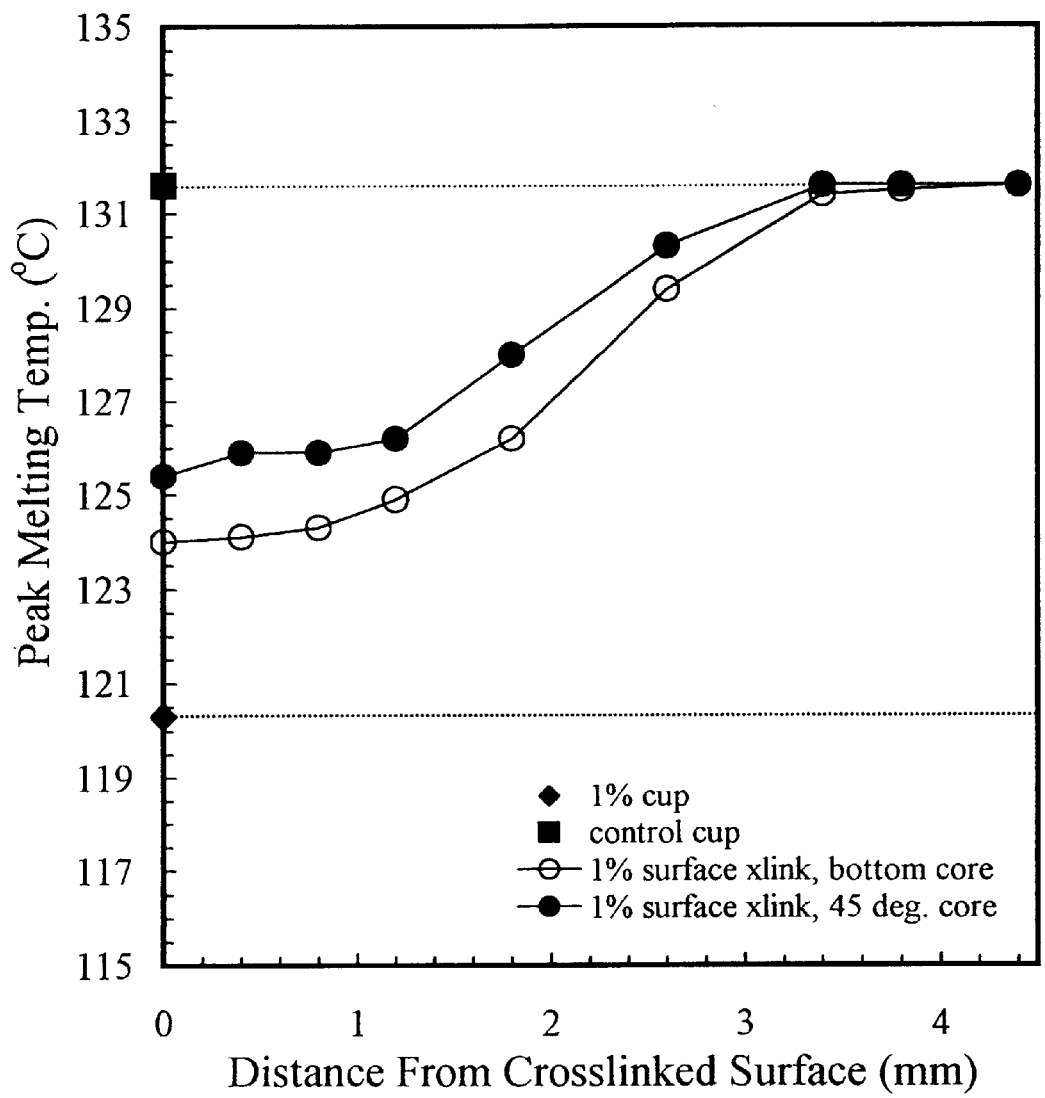
FIG. 17 graphically presents the profiles of peak melting temperature versus depth from the surface of a non-crosslinked cup (control) and for cups with surface layers crosslinked using 1% peroxide, comparing the profiles for cores taken from the bottom center of the cup and at 45 degrees from the bottom.

The melting temperatures as a function of depth are shown in FIG. 17. With peroxide crosslinking, in contrast to irradiated cups (EXAMPLE 5), where the melting temperature increases after crosslinking, the melting temperatures of the cups that were crosslinked with peroxide decreased after crosslinking, due to the specimens having recrystallized in a crosslinked melt. Thus, the higher the concentration of peroxide that is mixed with the polyethylene powder, the greater the resultant crosslinking, and the lower the melting temperature (FIG. 5). There was a strong gradient in melting temperature (i.e., a gradient in crosslink density) near the surface, reaching a plateau about 3 mm deep, indicating that the UHMWPE had little or no crosslinking deeper than about 3 mm (FIG. 17), as intended. Although the melting temperature profile was slightly lower for the core taken from the bottom center of the cup, the overall similarity of the profiles of the melting temperature indicated that the crosslinking was nearly uniform at different locations in the cup.

These results demonstrated that, simply by adjusting the concentration of peroxide that is mixed with the original UHMWPE powder and/or adjusting the the thickness of the layer of peroxide-mixed UHMWPE applied to the concave surface, the degree of crosslinking and/or the depth of penetration of the crosslinking into the bearing surface can be systematically modified by one skilled in the art.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allow for obvious changes in the basic invention herein are also within the claims.

We claim:

1. A surface-gradient crosslinked implant comprising a polyethylene bearing surface having a maximum gel content of from about 80 to about 100% within the bearing surface, the gel content gradually decreasing to about 50% of the bearing surface gel content at about 0.5 to about 2 mm from the bearing surface, and tapering to nearly zero by about 2 to about 3 mm from the bearing surface; the remainder of the implant remains uncrosslinked.

2. A method for improving the wear resistance of a bearing surface of an implant, wherein said bearing surface comprises polyethylene, the method comprises the step of subjecting the bearing surface of the implant which is fully formed to electron-beam radiation to crosslink the bearing surface, while the remainder of the implant that is not part of the bearing surface is not subjected to the electron-beam radiation and, therefore, remains uncrosslinked.

3. The method of claim 2, wherein the irradiated implant is further subjected to one or more of the following steps: (1) pressurization in hydrogen to reduce residual free radicals generated by the irradiation, (2) annealing or remelting the implant to reduce residual free radicals generated by the irradiation, (3) shaping the implant into a final shape, and (4) treating with ethylene oxide the irradiated implant, either in its original or final shape, to reduce residual free radicals generated by the irradiation.

4. The method of claim 3, wherein the shaping step comprises removing the most oxidized outer layer of the bearing surface of the irradiated implant.

5. A method for improving wear resistance of a bearing surface of an implant, wherein said bearing surface comprises polyethylene, the method comprising the step of crosslinking the polyethylene with a free radical generating chemical, during a process for making the implant so that the remainder of the implant, when made, that is not part of the bearing surface remains uncrosslinked, the resultant implant is termed a surface crosslinked implant.

6. The method of claim 5, further comprising one or more of the following steps of: (1) reducing residual chemicals resulting from the crosslinking process, (2) annealing the surface crosslinked implant at a temperature and for a time sufficient to stabilize its size, and (3) shaping the surface crosslinked implant into its final shape.

7. The method of claim 6, wherein the free radical generating agent is a peroxide.

8. The method of claim 6, wherein step (1) comprises soaking the surface crosslinked implant in a solvent to reduce the residual chemicals resulting from the crosslinking process.

9. The method of claim 6, wherein the shaping step comprises removing the outer most oxidized layer from the surface crosslinked implant.

10. A method for improving the wear resistance of a bearing surface of an implant, wherein said bearing surface comprises polyethylene, the method comprises the step of subjecting the bearing surface of the implant which is partially formed to electron-beam radiation to crosslink the bearing surface, while the remainder of the partially formed implant that is not part of the bearing surface is not subjected to the electron-beam radiation and, therefore, remains uncrosslinked.

11. The method of claim 10, wherein the irradiated partially formed implant is further subjected to one or more of the following steps: (1) pressurization in hydrogen to reduce residual free radicals generated by the irradiation, (2) annealing or remelting to reduce residual free radicals generated by the irradiation, (3) shaping the partially formed implant into a final shape, and (4) treating with ethylene oxide the irradiated partially formed implant, either in its original or final shape, to reduce residual free radicals generated by the irradiation.

12. The method of claim 11, wherein the shaping step comprises removing the most oxidized outer layer of the bearing surface of the irradiated partially formed implant.

13. An implant produced by any one of the foregoing methods of claims 2 to 12.

* * * * *